(12) United States Patent
Hagiwara

(10) Patent No.: US 6,865,247 B2
(45) Date of Patent: Mar. 8, 2005

(54) THREE DIMENSIONAL BACK PROJECTION METHOD AND AN X-RAY CT APPARATUS

(75) Inventor: Akira Hagiwara, Tokyo (JP)

(73) Assignee: GE Medical Systems Global Technology, LLC, Waukesha, WI (US)

( * ) Notice: Subject to any disclaimer, the term of this patent is extended or adjusted under 35 U.S.C. 154(b) by 135 days.

(21) Appl. No.: 10/442,611

(22) Filed: May 21, 2003

(65) Prior Publication Data

US 2003/0219093 A1 Nov. 27, 2003

(30) Foreign Application Priority Data

May 22, 2002 (JP) .......................................... 2002-147231
Nov. 6, 2002 (JP) .......................................... 2002-322756

(51) Int. Cl.[7] .................................................. A61B 6/03
(52) U.S. Cl. ................................. 378/4; 15/19; 15/901
(58) Field of Search .............................. 378/4, 8, 15, 19, 378/901

(56) References Cited

U.S. PATENT DOCUMENTS

| | | | |
|---|---|---|---|
| 4,149,247 A | 4/1979 | Pavkovich et al. | |
| 6,061,421 A | 5/2000 | Hagiwara | |
| 6,125,163 A | 9/2000 | Barth et al. | |
| 6,198,789 B1 * | 3/2001 | Dafni | 378/8 |
| 6,201,849 B1 | 3/2001 | Lai | |
| 6,324,246 B1 * | 11/2001 | Ruimi | 378/15 |
| 6,560,308 B1 | 5/2003 | Zmora | |
| 2004/0116797 A1 * | 6/2004 | Takahashi et al. | 600/407 |

* cited by examiner

*Primary Examiner*—David V Bruce
(74) *Attorney, Agent, or Firm*—Carl B. Horton, Esq.; Armstrong Teasdale LLP

(57) ABSTRACT

In order to reduce the amount of computation in the cone beam reconstruction, the invention provides, from within raw data acquired using a multidetector, extracting raw data Dr corresponding to plural lines on reconstruction field (S4), generating projection line data (S5) by multiplying raw data with cone beam reconstruction weight, filtering projection line data to generate image positional line data Df (S6), determining back projection pixel data (S7, S8, S9) of each pixel on the reconstruction field based on the image positional line data, adding, for each pixel, back projection pixel data of all views used for the image reconstruction to determine back projection data (S10, S11). The number of lines may be variable in compliance with a desired image quality.

24 Claims, 21 Drawing Sheets

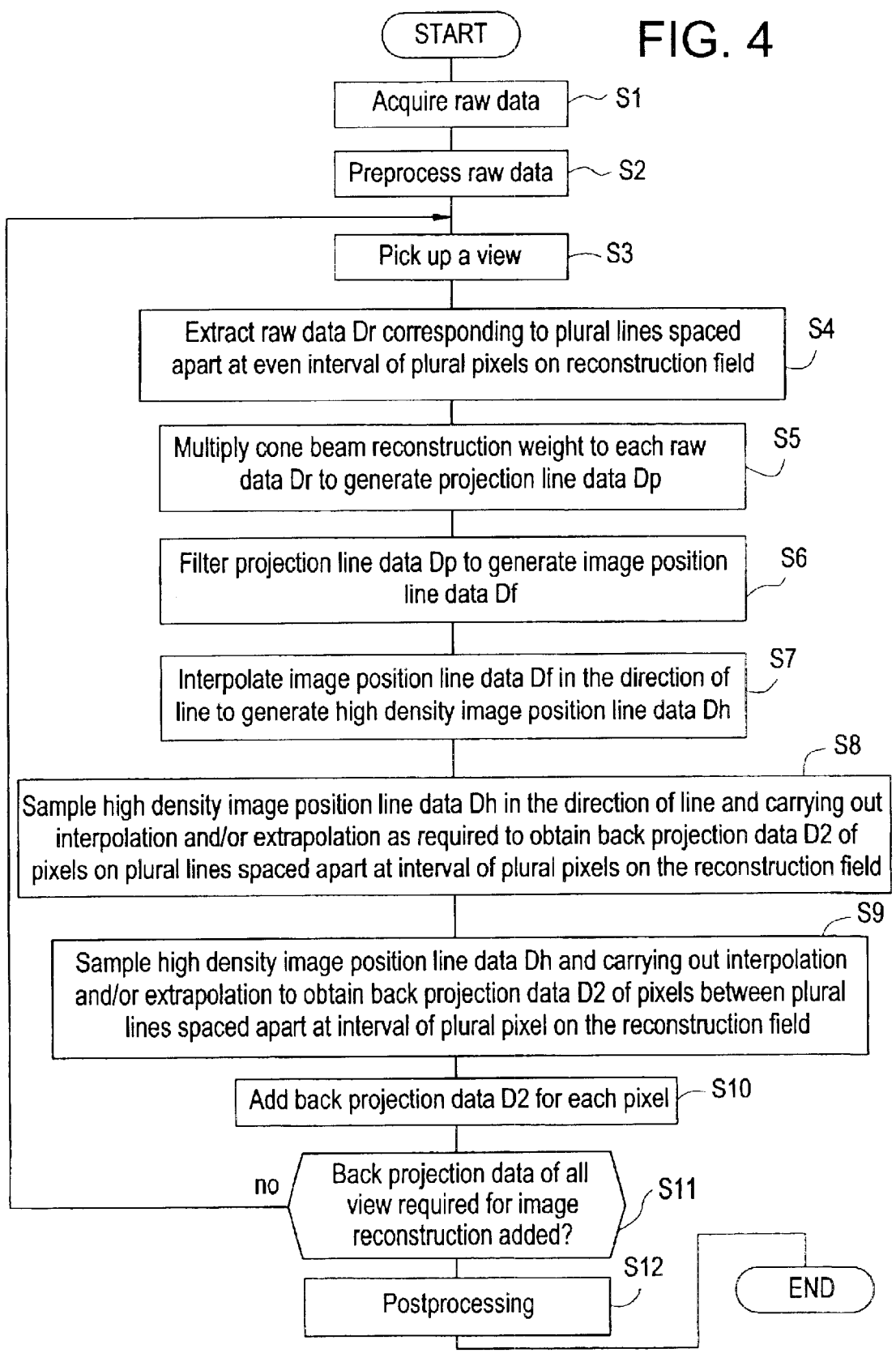

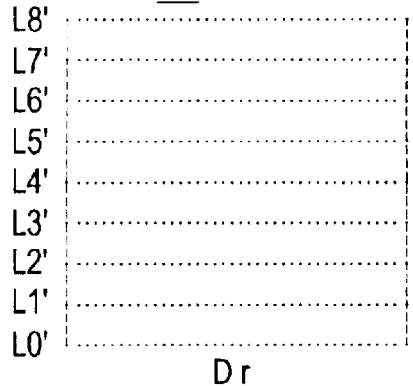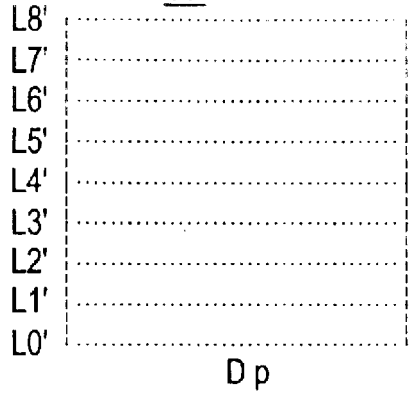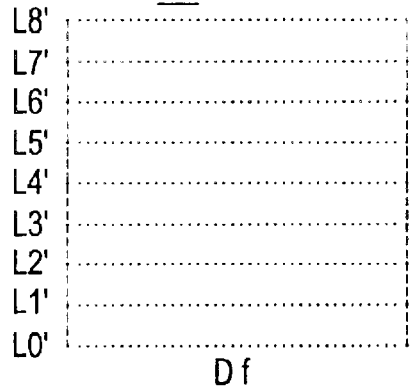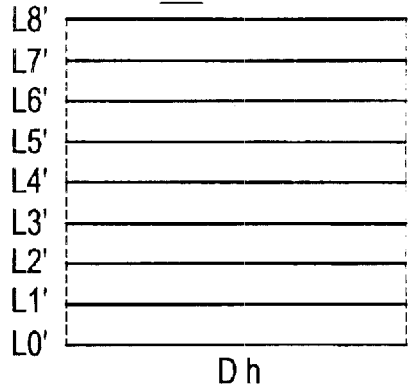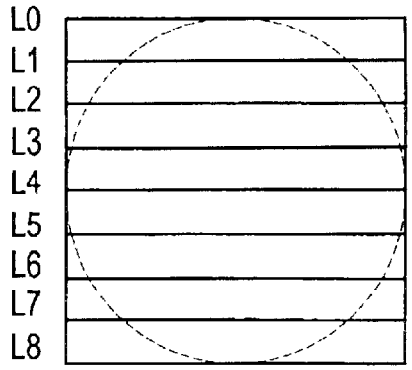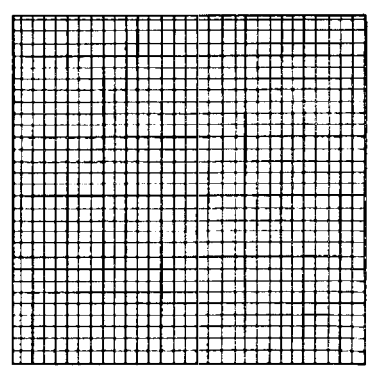

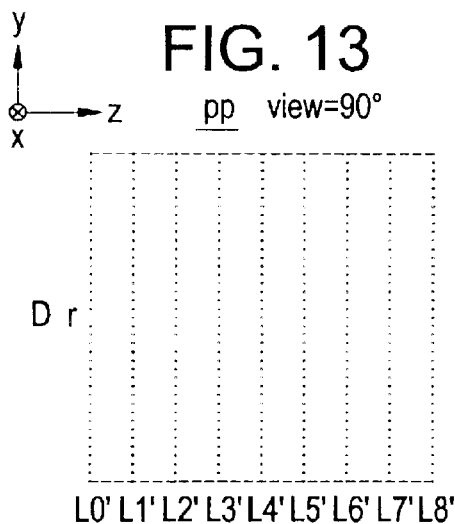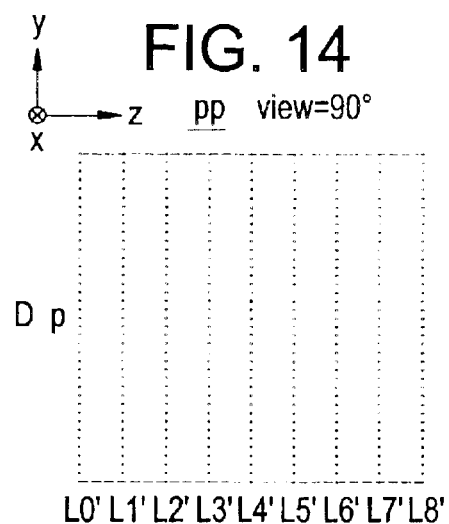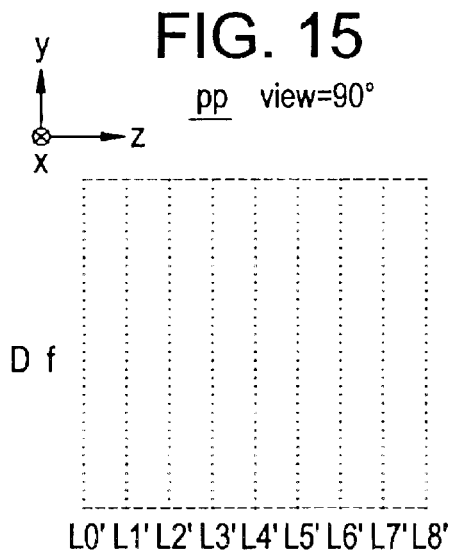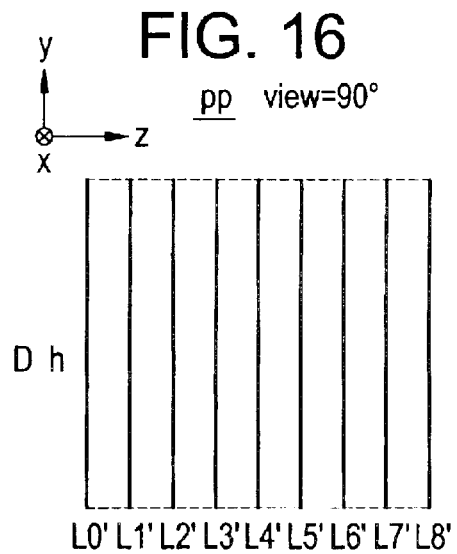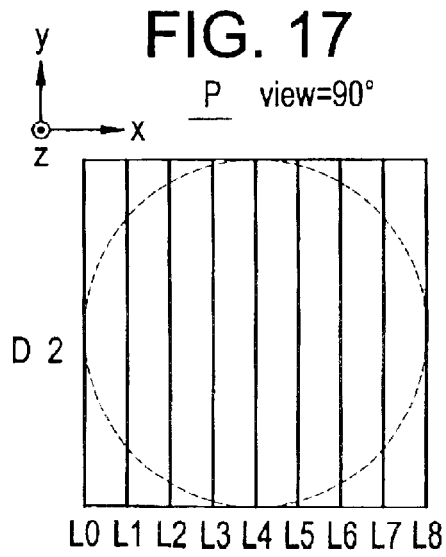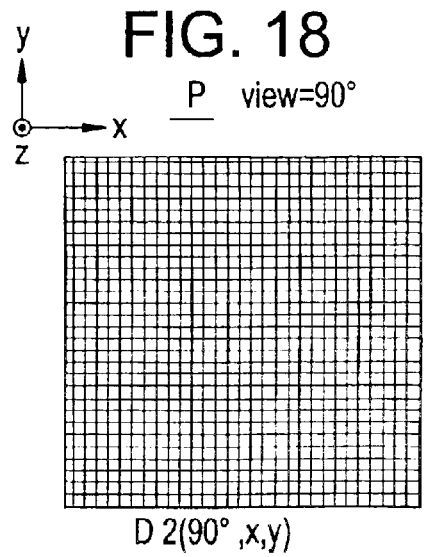

FIG. 23A
FIG. 23B
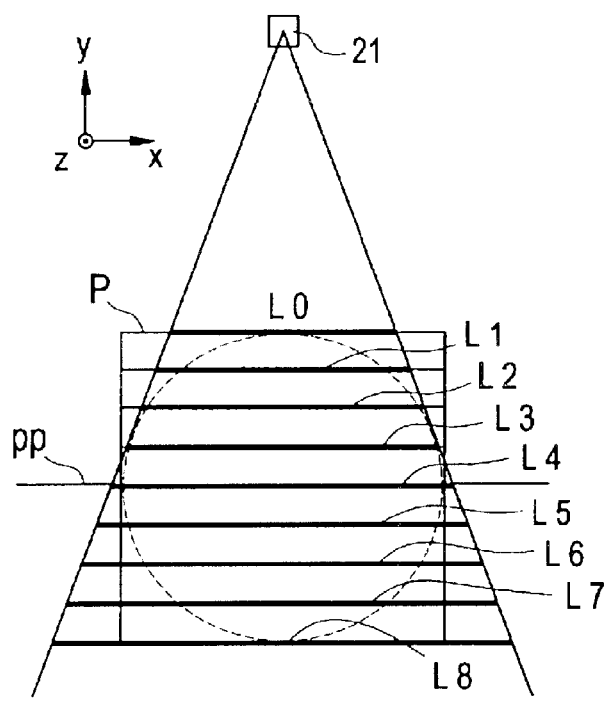
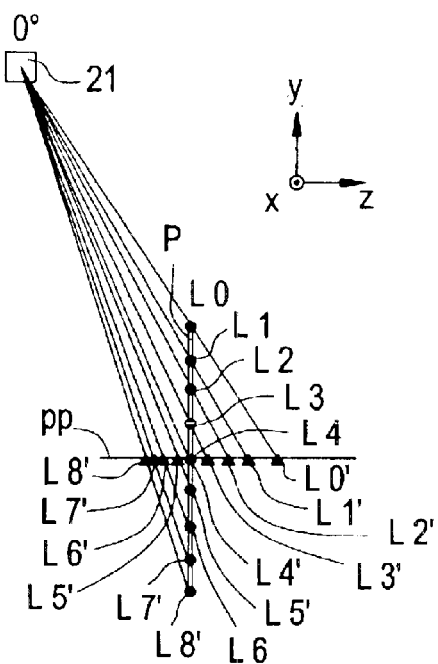
FIG. 24
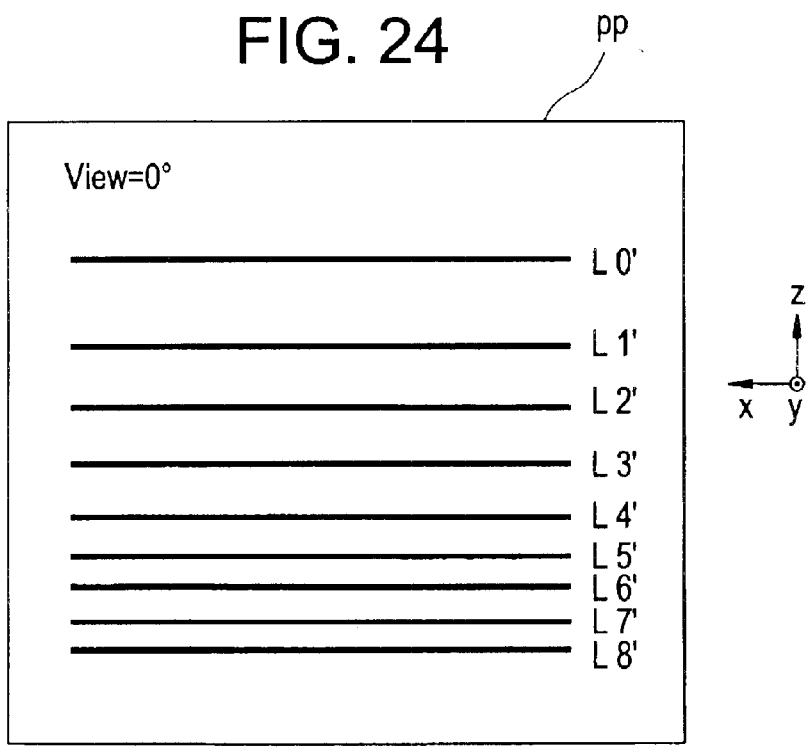

THREE DIMENSIONAL BACK PROJECTION METHOD AND AN X-RAY CT APPARATUS

CROSS REFERENCE TO RELATED APPLICATIONS

This application claims the benefit of Japanese Application No. 2002-147231 filed May 22, 2002, and Japanese Application No. 2002-322756 filed Nov. 6, 2002.

BACKGROUND OF THE INVENTION

The present invention is directed to three dimensional back projection method and an X-ray CT (computed tomography) apparatus, more specifically to three dimensional back projection method and an X-ray CT apparatus allowing the computation to be decreased by the image reconstruction based on the projection data obtained by the axial scan or helical scan using a multidetector (referred to as "cone beam reconstruction").

Current mainstream X-ray CT apparatuses uses filtered back projection scheme for reconstruction of a CT image through data capturing, preprocessing, filtering, back projecting and postprocessing.

In the filtering, FFT operation is performed on the raw data, which is then multiplied by a reconstruction function in a frequency domain and thereafter reverse FFT operation is performed thereon.

Related Prior Art is disclosed in Japanese Published Unexamined Patent Application No. S59-168840.

Recently, X-ray CT apparatuses using a multidetector having a number of detector arrays are being developed.

The raw data obtained by using such a multidetector may have a huge data size, causing a problem that the FFT operation in the filtering may become huge. For example, in case of a multidetector having 256 detector arrays, there is a problem that at least 256 FFT operations are needed for every view.

SUMMARY OF THE INVENTION

The object of the present invention is therefore to provide three dimensional back projection method and an X-ray CT apparatus allowing the operation to be decreased, in the so-called cone beam reconstruction.

In a first aspect, the present invention provides a three dimensional back projection method, comprising the steps of: extracting raw data Dr each corresponding to one or a plurality of parallel lines on a reconstruction field, from within raw data gathered by an axial scan or helical scan by means of a multidetector having a plurality of detector arrays; generating projection line data Dp by multiplying said raw data Dr by the cone beam reconstruction weight; generating field positional line data Df of an image by performing a filter operation on the projection line data Dp; determining back projection pixel data D2 of each pixel on the reconstruction field based on the each positional line data Df of an image; and determining a back projection data D3 by adding, for each corresponding pixel, back projection pixel data D2 of all of views used for the image reconstruction.

In the three dimensional back projection method according to the first aspect above, raw data Dr corresponding to one or a plurality of parallel lines on the reconstruction field is extracted and then filtering is performed solely thereon, so that the number of FFT operation in the filtering may be significantly decreased. For example, there are nine lines, FFT operation may be sufficient only nine times for each view.

If the number of lines is one, then the number of operation may be identical to that of conventional two dimensional back projection without cone beam compensation.

In a second aspect, the present invention provides a three dimensional back projection method according to the arrangement as have been described above, characterized in that the number of said plurality of lines is in the range from 1/512 to 1/1 of the maximum number of pixels in the reconstruction field in the direction perpendicular to the lines.

The three dimensional back projection method according to the second aspect above, by setting the number of plural lines to the range from 1/512 to 1/1 of the maximum number of pixels in the reconstruction field in the direction perpendicular to the lines, saving efficiency of processing time and degradation of image quality may be appropriately balanced. More specifically, when the ratio of line number is approaching to 1/512, effect of shortening the processing time may be improved while the image quality will be degraded. On the other hand when the ratio of line number is approaching to 1/1, the effect of shortening the processing time may be less effective. It is to be noted that if the ratio of line number becomes 1/1, then the process will be identical to that without the interpolation in the direction normal to the lines.

In a third aspect, the present invention provides a three dimensional back projection method according to the arrangement as have been described above, characterized in that, when defining z-axis as the direction perpendicular to the revolving plane of an X-ray tube or multidetectors or as the direction of linear translation of the helical scan, y-axis as the direction of center axis of the X-ray beam at view=0°, and x-axis as the direction perpendicular to both z-axis and y-axis; x-axis becomes line direction in the range of view angle of −45°≦view<45° or in the range mainly composed thereof and including therearound, and in the range of view angle of 135°≦view<225° or the range mainly composed thereof and including therearound; and y-axis becomes line direction in the range of view angle of 45°≦view<135° or the range mainly composed thereof and including therearound, and in the range of view angle of 225°≦view 315° or the range mainly composed thereof and including therearound.

It should be noted here that although in the present specification, view=45° and view=315° are differently designated for the sake of explanation, these are identical and same view in practice.

When determining data of lines on the reconstruction field, the precision will be higher if the angle between the line and the detector plane is approaching to the parallel, and the precision will be lower if the angle is approaching to the perpendicular.

In the three dimensional back projection method according to the third aspect above, as the angle between the line and the detector plane may not become less than approximately 45°, the degradation of precision may be controllably fall into the tolerance.

In a fourth aspect, the present invention provides a three dimensional back projection method according to the arrangement as have been described above, further including the steps of: generating high density positional line data Dh of an image by interpolating or extrapolating the positional line data Df of an image in the direction of scan line; and determining back projection pixel data D2 of each pixel on the reconstruction field by sampling and interpolating or extrapolating when required the high density positional line data Dh of an image.

The three dimensional back projection method according to the fourth aspect above, as compared to the pixel density in the reconstruction field, data density in the direction of lines can be produced much higher. Thereby the major part of the process of determining back projection pixel data D2 by projecting data Dh onto the reconstruction field in the direction of X-ray transmission is allowed being only sampling, resulting in simplified and much faster processing. However, interpolation and/or extrapolation may be inserted as needed.

It is to be noted here that the interpolation and/or extrapolation may be selected from any of interpolation and/or extrapolation of 0th order (copy of the nearest data), interpolation and/or extrapolation of 1st order, or interpolation and/or extrapolation of 2nd order or higher (e.g., Hanning interpolation or Cubic interpolation).

In a fifth aspect, the present invention provides a three dimensional back projection method according to the arrangement as have been described above, further comprising the step of: when extracting raw data Dr each corresponding to one of a plurality of parallel lines spaced apart at an even interval of a plurality of pixels on the reconstruction field from within raw data at a given view angle, if part or all of the corresponding raw data is not present, computing the corresponding raw data Dr by performing interpolation and/or extrapolation by means of adjacent raw data.

When the reconstruction field is located at the proximity of the edge of the multidetector, there may be cases in which no raw data Dr exists corresponding to a plurality of parallel lines spaced apart at an even interval of a plurality of pixels on the reconstruction field.

In the three dimensional back projection method according to the fifth aspect above, the corresponding raw data Dr may be computed by performing interpolation and/or extrapolation by means of raw data present at the proximity of the location to which a plurality of parallel lines spaced apart at an even interval of a plurality of pixels on the reconstruction field are projected on the detector plane or virtual projection plane in the direction of X-ray transmission. Thereby the method may process data even when the reconstruction field is located at the proximity of the edge of the multidetector.

In a sixth aspect, the present invention provides a three dimensional back projection method according to the arrangement as have been described above, further comprising the step of: when extracting raw data Dr each corresponding to one of a plurality of parallel lines spaced apart at an even interval of a plurality of pixels on the reconstruction field from within raw data at a given view angle, if part or all of the corresponding raw data is not present, computing the raw data corresponding to the reconstruction field by performing interpolation and/or extrapolation by means of adjacent raw data to extract the raw data Dr corresponding to a plurality of lines from within thus computed raw data.

If the reconstruction field is located at the proximity of the edge of the multidetector, there may be cases in which no raw data Dr exists corresponding to a plurality of parallel lines spaced apart at an even interval of a plurality of pixels on the reconstruction field.

In the three dimensional back projection method according to the sixth aspect, interpolation and/or extrapolation of a plurality of parallel lines spaced apart at an even interval of a plurality of pixels on the reconstruction field by using raw data present at the proximity of the projected point on the multidetector plane or on the virtual projection plane in the direction of X-ray transmission, may allow computing raw data in the domain corresponding to the reconstruction field. The method may thereby process data even when the reconstruction field is located at the proximity of the edge of the multidetector.

In a seventh aspect, the present invention provides a three dimensional back projection method according to the arrangement as have been described above, in which the field corresponding to the reconstruction field is the field to which a circular field or square field on the reconstruction plane is projected in the direction of X-ray projection.

The reconstruction field may be either a circular field through which X-ray beam may pass at every view angles, or a square field, which circumscribes the circular field.

The three dimensional back projection method according to the seventh aspect above may process data in either cases.

In an eighth aspect, the present invention provides a three dimensional back projection method according to the arrangement above, further comprising the steps of: performing interpolation and/or extrapolation of raw data in a given view angle to generate high density raw data in the direction of the detector array of multidetector; and extracting the raw data Dr corresponding to a plurality of parallel lines spaced apart at an even interval of a plurality of pixels on the reconstruction field from within the high density raw data in the direction of detector array.

When reconstructing a CT image for a plurality of reconstruction fields, although raw data corresponding to a plurality of parallel lines spaced apart at an even interval of a plurality of pixels on the reconstruction field may be determined for each of reconstruction fields, the raw data determined in a reconstruction field may not be used in any other reconstruction fields.

In contrast, the three dimensional back projection method according to the eighth aspect above, since high density raw data may be generated by means of interpolation and/or extrapolation in the direction of detector arrays of the multidetector, raw data Dr corresponding to a plurality of parallel lines spaced apart at an even interval of a plurality of pixels on the reconstruction field may be obtained by sampling when reconstructing a CT image for a plurality of reconstruction fields. In addition, if a reconstruction field is added after sampling, the high density raw data in the detector direction may be reused.

It is to be noted here that the interpolation and/or extrapolation may be selected from any of interpolation and/or extrapolation of 0th order (copy of the nearest data), interpolation and/or extrapolation of 1st order, or interpolation and/or extrapolation of 2nd order or higher (e.g., Hanning interpolation or Cubic interpolation).

In a ninth aspect, the present invention provides a three dimensional back projection method according to the arrangement as have been described above, in which interpolation and/or extrapolation is performed such that the raw data has the density two to four times higher than the density in the direction of detector array of raw data at a given view angle.

When increasing the density of raw data by performing interpolation and/or extrapolation in the direction of detector arrays of the multidetector, if the density is overly higher then the effect of shortening processing time will decrease, and if the density is insufficiently increased the image quality will be degraded.

The three dimensional back projection method according to the ninth aspect above, interpolation and/or extrapolation increases the density of actually present raw data in the range from 2 to 4 times higher of the density in the direction of detector arrays to appropriately match the shortening effect of processing time with the degradation of image quality.

In a tenth aspect, the present invention provides a three dimensional back projection method according to the arrangement as have been described above, in which the number of lines in said plurality of lines may be varied according to the image quality specified by an operator.

In general, the image quality will be improved when the line density projected on the detector plane from a plurality of lines on the reconstruction field is higher. However the amount of data computation will be accordingly increased.

The three dimensional back projection method according to the tenth aspect as have been described above, the number of plural lines on the reconstruction field may be adjusted according to the image quality specified by the operator. The amount of data computation thereby will be optimized with respect to the desired image quality.

In an eleventh aspect, the present invention provides a three dimensional back projection method according to the arrangement above, in which the number of lines in the plurality of lines may be varied according to the distance from the center of the detector array to the reconstruction field.

In case in which the number of lines on the reconstruction field is fixed, the line density projected to the detector plane from the plural lines on the reconstruction field will be decreased for larger distance from the center of the detector array to the reconstruction field (lines will be more spaced apart each from other), while on the other hand the line density projected to the detector plane from the plural lines on the reconstruction field will be increased for shorter distance from the center of the detector array to the reconstruction field (lines will be approaching each to other). However, the image quality will be degraded if the density of projected lines on the detector plane is too sparse. Also the amount of computation will be tremendously increased if the line density projected to the detector plane is too dense (image quality will not be proportionally improved as compared to the increment of the amount of computation).

Thus in the three dimensional back projection method according to the eleventh aspect, the number of plural lines on the reconstruction field will be adjusted according to the distance from the center of the detector array to the reconstruction field. This allows the line density projected on the detector plane to be always appropriate (the amount of data computation will be optimal for a desired image quality).

In a twelfth aspect, the present invention provides a three dimensional back projection method according to the arrangement as have been described above, in which the number of lines in said plurality of lines may be varied according to the view.

In case in which the number of lines on the reconstruction field is fixed, when the reconstruction field is placed offset from the revolving center for example, for a view with the X-ray tube located in the offset side, the line density projected to the detector plane of the plural lines on the reconstruction field will be lower (lines spaced apart each from other), and for a view with the X-ray tube located in the direction opposed to the offset, the line density projected on the detector plane of the plural lines on the reconstruction field will be higher (lines adjoining each to other) However, the image quality will be degraded if the line density projected to the detector plane becomes too sparse. In addition, if the line density projected to the detector plane is too dense the amount of computation will be tremendously increased (image quality will not be proportionally improved as compared to the increment of the amount of computation).

Thus in the three dimensional back projection method according to the twelfth aspect above, the number of lines on the reconstruction field will be adjusted for each view. Thereby the line density projected on the detector plane will be always optimal (optimal amount of computation will be yielded for a desired quality).

In a thirteenth aspect, the present invention provides an X-ray CT apparatus that comprises: an X-ray tube; a multidetector having a plurality of detector array; a scanner means by rotating or revolving around the object at least one of the X-ray tube or the multidetector while moving linearly both means through a relative trajectory with respect to the object, for gathering raw data; a raw data extractor means for extracting raw data Dr each corresponding to one or a plurality of parallel lines on a reconstruction field from within the raw data; a cone beam reconstruction weight multiplier means for multiplying the raw data Dr to a cone beam reconstruction weight to generate projected line data Dp; a filter means for filtering the projection line data Dp to generate positional line data Df of an image; a back projection pixel data obtaining means for determining back projection pixel data D2 of each pixel on the reconstruction field based on the positional line data Df of an image; and a back projection data computing means for determining back projection data D3 by adding for each pixel back projection data D2 of all views used for reconstructing an image.

The X-ray CT apparatus according to the thirteenth aspect as have been described above may preferably carry out the three dimensional back projection method according to the first aspect described above.

In a fourteenth aspect, the present invention provides an X-ray CT apparatus according to the arrangement as have been described above, in which the number of the plurality of lines is in the range from 1/512 to 1/1 of the maximum number of pixels in the reconstruction field in the direction perpendicular to the lines.

The X-ray CT apparatus according to the fourteenth aspect described above may preferably carry out the three dimensional back projection method according to the second aspect described above.

In a fifteenth aspect, the present invention provides an X-ray CT apparatus, in which: when defining z-axis as the direction perpendicular to the revolving plane of an X-ray tube or multidetectors or as the direction of linear translation of the helical scan, y-axis as the direction of center axis of the X-ray beam at view=0° and x-axis as the direction perpendicular to both z-axis and y-axis; x-axis becomes line direction in the range of view angle of $-45° \leq view < 45°$ or in the range mainly composed thereof and including therearound, and in the range of view angle of $135° \leq view < 225°$ or the range mainly composed thereof and including therearound; and y-axis becomes line direction in the range of view angle of $45° \leq view < 135°$ or the range mainly composed thereof and including therearound, and in the range of view angle of $225° \leq view < 315°$ or the range mainly composed thereof and including therearound.

The X-ray CT apparatus according to the fifteenth aspect as have been described above may preferably carry out the three dimensional back projection method according to the third aspect above.

In a sixteenth aspect, the present invention provides an X-ray CT apparatus according to the arrangement as have been described above, which further comprises: a line direction interpolation and/or extrapolation means for performing interpolation and/or extrapolation in the direction of lines on the positional line data Df of an image to generate high density positional line data of an image Dh; and wherein the back projection pixel data obtaining means performs sampling of the high density positional line data Dh of an image as well as interpolation and/or extrapolation to determine back projection pixel data D2 of each pixel on the reconstruction field.

The X-ray CT apparatus according to the sixteenth aspect above may preferably carry out the three dimensional back projection method set forth in the fourth aspect described above.

In a seventeenth aspect, the present invention provides an X-ray CT apparatus according to the arrangement as have been described above, which further comprises: an interpolation and/or extrapolation processing means, for use when extracting raw data Dr corresponding to a plurality of parallel lines spaced apart at an even interval of a plurality of pixels on the reconstruction field from within raw data of a given view angle, if part or all of the corresponding raw data is not present, operable for computing the corresponding raw, data Dr by performing interpolation and/or extrapolation by means of adjacent raw data.

The X-ray CT apparatus according to the seventeenth aspect described above may preferably carry out the three dimensional back projection method set forth in the fifth aspect described above.

In an eighteenth aspect, the present invention provides an X-ray CT apparatus according to the arrangement as have been described above, which further comprises: an interpolation and/or extrapolation processing means for use when extracting raw data Dr each corresponding to one of a plurality of parallel lines spaced apart at an even interval of a plurality of pixels on the reconstruction field from within raw data at a given view angle, if part or all of the raw data in the area corresponding to the reconstruction field is not present, computing the raw data corresponding to the reconstruction field by performing interpolation and/or extrapolation by means of adjacent raw data to extract the raw data Dr corresponding to a plurality of lines from within thus computed raw data; and wherein the raw data extractor means extracts the raw data Dr corresponding to a plurality of lines from within the computed raw data.

The X-ray CT apparatus according to the eighteenth aspect described above may preferably carry out the three dimensional back projection method according to the sixth aspect described above.

In a nineteenth aspect, the present invention provides an X-ray CT apparatus according to the arrangement as have been described above, in which the field corresponding to the reconstruction field is the field to which a circular field or square field on the reconstruction plane is projected in the direction of X-ray projection.

The X-ray CT apparatus according to the nineteenth aspect described above may preferably carry out the three dimensional back projection method according to the seventh aspect described above.

In a twentieth aspect, the present invention provides an X-ray CT apparatus according to the arrangement as have been described above, which further comprises: a detector array direction interpolation and/or extrapolation processing means for performing interpolation and/or extrapolation of raw data at a given view angle to generate high density raw data in the direction of detector array of the multidetector; wherein the raw data extracting means extracts raw data Dr corresponding to a plurality of parallel lines spaced apart at an even interval of a plurality of pixels on the reconstruction field from within the high density raw data in the direction of detector array.

The X-ray CT apparatus according to the twentieth aspect described above may preferably carry out the three dimensional back projection method according to the eighth aspect described above.

In a twenty first aspect, the present invention provides an X-ray CT apparatus according to the arrangement described above, in which the detector array direction interpolation and/or extrapolation processing means performing interpolation and/or extrapolation, which is such that the raw data has the density two to four times higher than the density in the direction of detector array of raw data at a given view angle.

The X-ray CT apparatus according to the twenty first aspect described above may preferably carry out the three dimensional back projection method according to the ninth aspect described above.

In a twenty second aspect, the present invention provides an X-ray CT apparatus according to the arrangement described above, in which said apparatus further comprises a line count setting means for varying the number of lines in the plurality of lines according to the image quality specified by an operator.

The X-ray CT apparatus according to the twenty second aspect described above may preferably carry out the three dimensional back projection method according to the tenth aspect described above.

In a twenty third aspect, the present invention provides an X-ray CT apparatus according to the arrangement described above, in which said apparatus further comprises a line count setting means for varying the number of lines in the plurality of lines according to the distance from the center of the detector array to the reconstruction field.

The X-ray CT apparatus according to the twenty third aspect described above may preferably carry out the three dimensional back projection method according to the eleventh aspect described above.

In a twenty fourth aspect, the present invention provides an X-ray CT apparatus according to the arrangement described above, in which said apparatus further comprises a line count setting means for varying the number of lines in the plurality of lines according to the view.

The X-ray CT apparatus according to the twenty fourth aspect described above may preferably carry out the three dimensional back projection method according to the twelfth aspect described above.

According to the three dimensional back projection method and X-ray CT apparatus of the present invention, the amount of computation for cone beam reconstruction may be reduced. In particular the amount of FFT computation in filtering may be significantly decreased.

Further objects and advantages of the present invention will be apparent from the following description of the preferred embodiments of the invention as illustrated in the accompanying drawings.

BRIEF DESCRIPTION OF THE DRAWINGS

FIG. 4 shows a schematic flow diagram of the operation of X-ray CT apparatus according to the first embodiment.

FIG. 7 shows a schematic diagram of the projection of raw data Dr of each line onto the projection plane at view=0°.

FIG. 8 shows a schematic diagram of the projection of projected line data Dp of each line onto the projection plane at view=0°.

FIG. 9 shows a schematic diagram of the projection of image positional line data Df of each line to the projection plane at view=0°.

FIG. 10 shows a schematic diagram of the projection of high density image positional line data Dh of each line to the projection plane at view=0°.

FIG. 11 shows a schematic diagram of the projection of back projection pixel data D2 of each line on the reconstruction field at view=0°.

FIG. 12 shows a schematic diagram of the projection of back projection pixel data D2 of each pixel on the reconstruction field at view=0°.

FIG. 13 shows a schematic diagram of the projection of raw data Dr of each line onto the projection plane at view=90°.

FIG. 14 shows a schematic diagram of the projection of projection line data Dp of each line onto the projection plane at view=90°.

FIG. 15 shows a schematic diagram of the projection of image positional line data Df of each line onto the projection plane at view=90°.

FIG. 16 shows a schematic diagram of the projection of high density image positional line data Dh of each line onto the projection plane at view=90°.

FIG. 17 shows a schematic diagram of back projection pixel data D2 of each line on the reconstruction field at view=90°.

FIG. 18 shows a schematic diagram of back projection pixel data D2 of each pixel on the reconstruction field at view=90°.

FIG. 23 shows a schematic diagram of the data absent zone of raw data projected onto the projection plane, the zone filled by raw data computed by the interpolation and/or extrapolation.

FIG. 24 shows a schematic diagram of the projection of lines on the reconstruction field to the projection plane in the direction of X-ray transmission.

DETAILED DESCRIPTION OF THE INVENTION

The present invention will be described hereinbelow in greater details with reference to embodiments illustrated in the accompanying drawings.

First Embodiment

Figure 1:
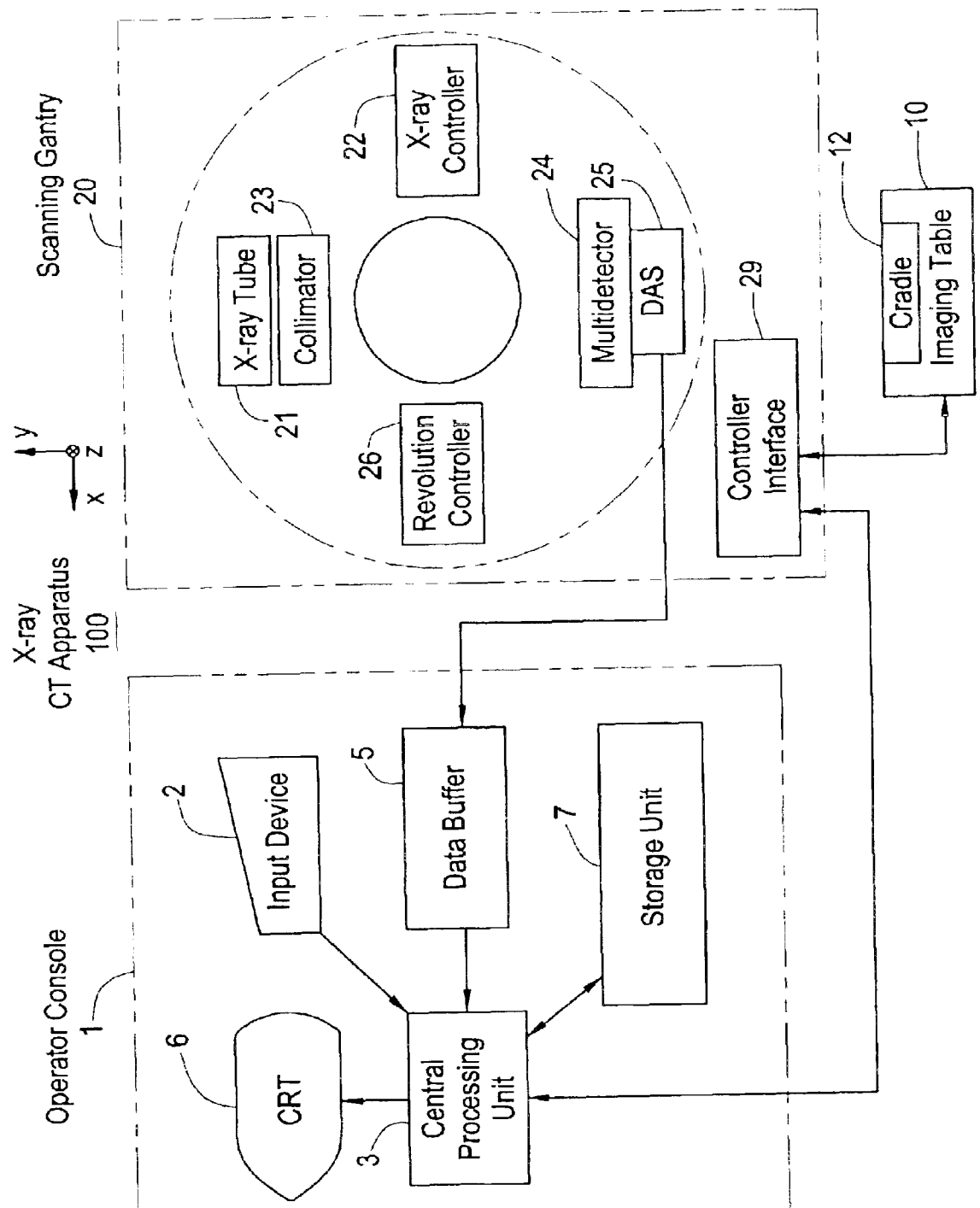
FIG. 1 shows a schematic block diagram of an X-ray CT apparatus according to a first embodiment of the present invention.

FIG. 1 shows a schematic block diagram of an X-ray CT apparatus according to a first embodiment of the present invention.

The X-ray CT apparatus 100 has an operator console 1, an imaging table 10, and a scanning gantry 20.

The operator console 1 includes an input device 2 for accepting input from an operator, a central processing unit 3 for executing three dimensional back projection process according to the present invention, a data buffer 5 for storing projection data obtained from the scanning gantry 20, a CRT 6 for displaying a CT image reconstructed from the projection data, and a storage unit 7 for storing such programs, data, as well as X-ray CT images.

The imaging table 10 includes a cradle 12 for carrying in and out the object to be imaged into and out of the bore (central void) of the scanning gantry 20. The cradle 12 may be driven by a motor incorporated in the imaging table 10.

The scanning gantry 20 includes an X-ray tube 21, an X-ray controller 22, a collimator 23, a multidetector 24, a data acquisition system (DAS) 25, a revolving controller 26 for moving the X-ray tube 21 around the body axis of the object, and a controller interface 29 for sending and receiving control signals to and from the operator console 1 and imaging table 10.

Figure 2:
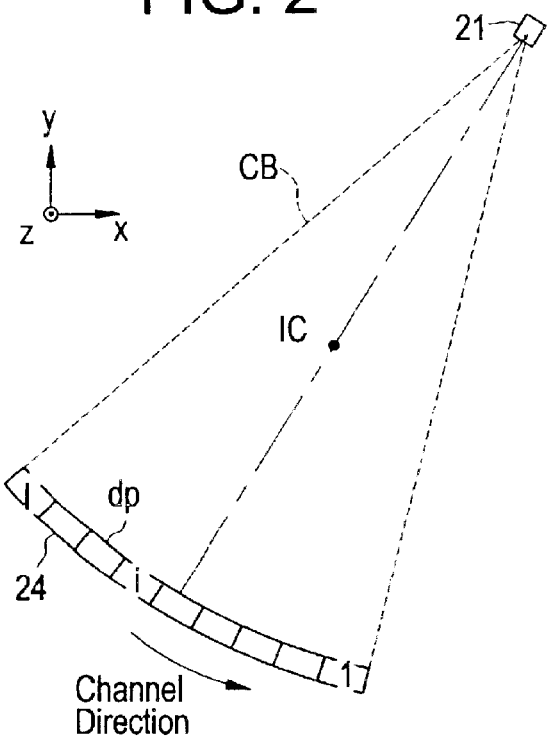
FIG. 2 shows a schematic diagram of revolution of an X-ray tube and multidetector.
Figure 3:
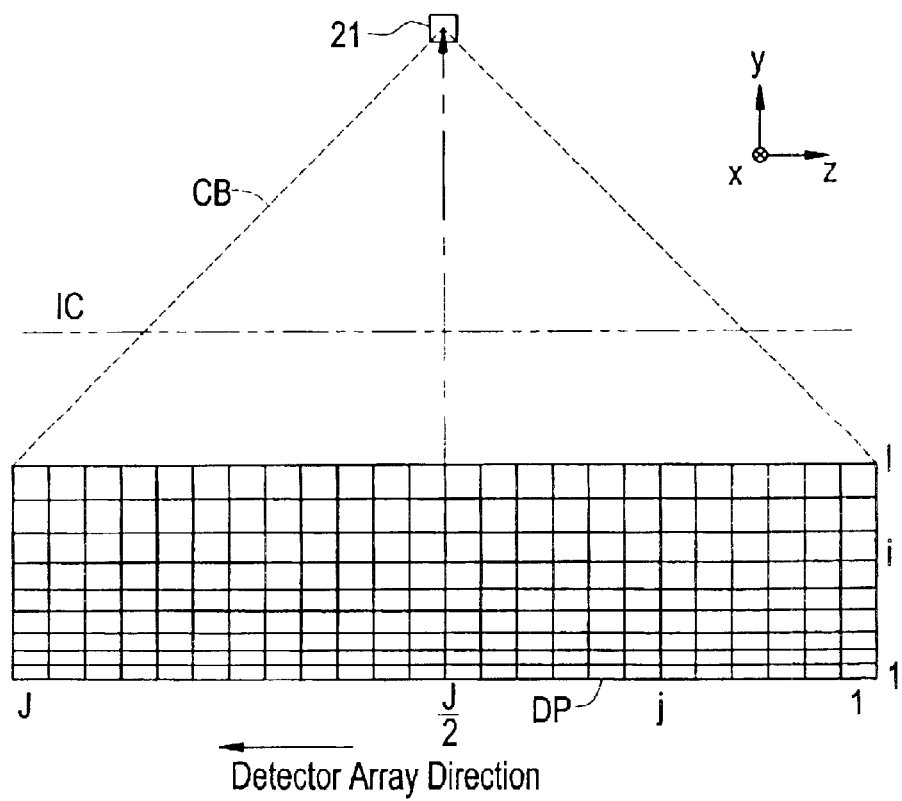
FIG. 3 shows a schematic diagram of cone beam.

FIG. 2 and FIG. 3 show schematic diagrams of an X-ray tube 21 and a multidetector 24.

The X-ray tube 21 and multidetector 24 may revolve around the revolving center IC. Here the vertical direction is denoted as y axis, horizontal direction as x axis, the direction perpendicular to those two directions as z axis, the revolution plane of the X-ray tube 21 and multidetector 24 maybe in the x-y plane. The displacement direction of the cradle 12 is in z axis.

The X-ray tube 21 generates X-ray beam referred to as cone beam CB. The angle of view=0° when the center axis of cone beam CB is in parallel to y direction.

The multidetector 24 may have for example 256 detector arrays. In addition each detector array may have for example 1024 channels.

In the following description the helical scan is assumed. The present invention may be equally applied to the axial scan, similar to the helical scan, except that the cradle 12 will not move linearly.

FIG. 4 illustrates a flow diagram indicating schematic operation of X-ray CT apparatus 100.

In step S1, by revolving the X-ray tube 21 and multidetector 24 around the object to be imaged and at the same time linearly moving the cradle 12, raw data D0 (view, δ, j, i) will be acquired, where view is the view angle, d is relative angle, j is the number of detector array, i is the number of channel.

The relative angle d is a parameter indicating how many round the current view is at the same view angle, e.g., δ=0° for the first round, δ=360° for the second round, δ=720° for the third round, and so on.

In step S2, preprocessing (offset compensation, logarithm compensation, X-ray radiation compensation, sensitivity compensation) will be carried out for the raw data D0 (view, δ, j, i).

In step S3, one of all views required for the reconstruction of a CT image (views for 360° or views for 180° plus fan angle) will be selected.

In step S4, from within raw data of the selected view, raw data Dr corresponding to a plurality of parallel lines spaced apart at an even interval of plural pixels on the reconstruction field will be extracted.

Figure 5A:
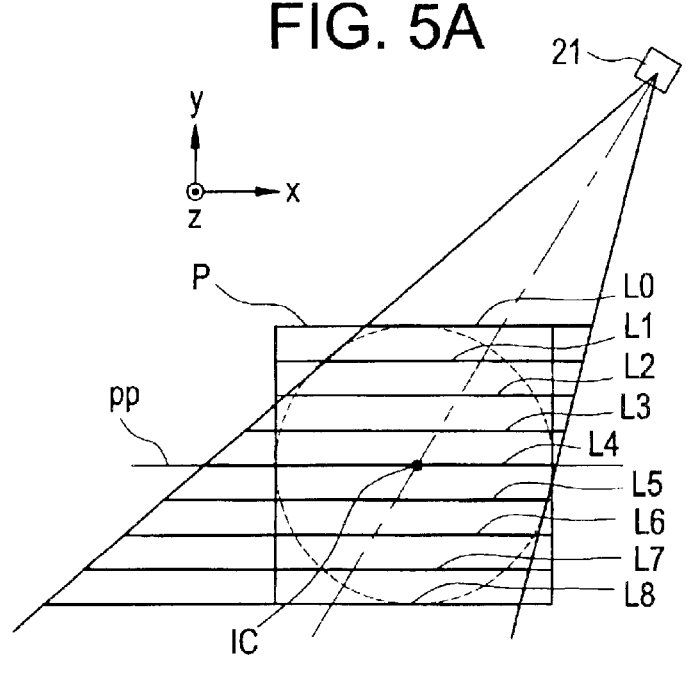
FIG. 5 shows a schematic diagram of the projection of line on the reconstruction field to the direction of X-ray transmission.
Figure 5B:
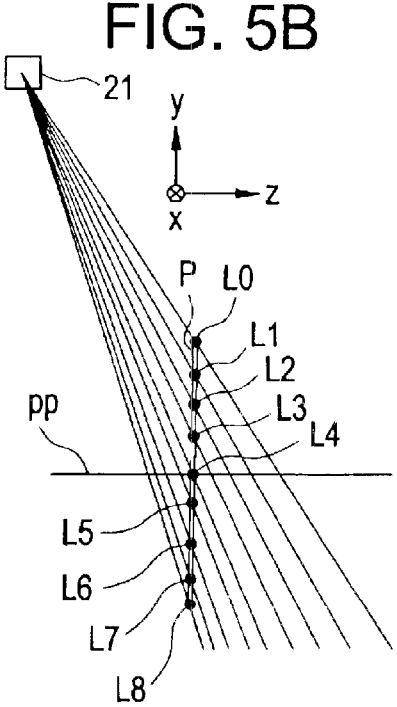

In FIG. 5, a plurality of parallel lines L0 to L8 are depicted on the reconstruction field P.

The number of lines may be 1/64 through 1/2 of the maximum number of pixels on the reconstruction field in the direction perpendicular to the lines. For example, when the number of pixels on the reconstruction field P is 512 by 512 pixels, the number of lines will be 9.

When $-45° \leq \text{view} < 45°$ (or a view angle range mainly composed thereof and including therearound) and $135° \leq \text{view} < 225°$ (or a view angle range mainly composed thereof and including therearound), x axis should be the line direction. When $45° \leq \text{view} < 135°$ (or a view angle range mainly composed thereof and including therearound) and $225° \leq \text{view} < 3150$ (or a view angle range mainly composed thereof and including therearound), y axis should be the line direction.

There is also a projection plane pp assumed to be in parallel to those lines L0 to L8, through the revolution center IC.

Figure 6:
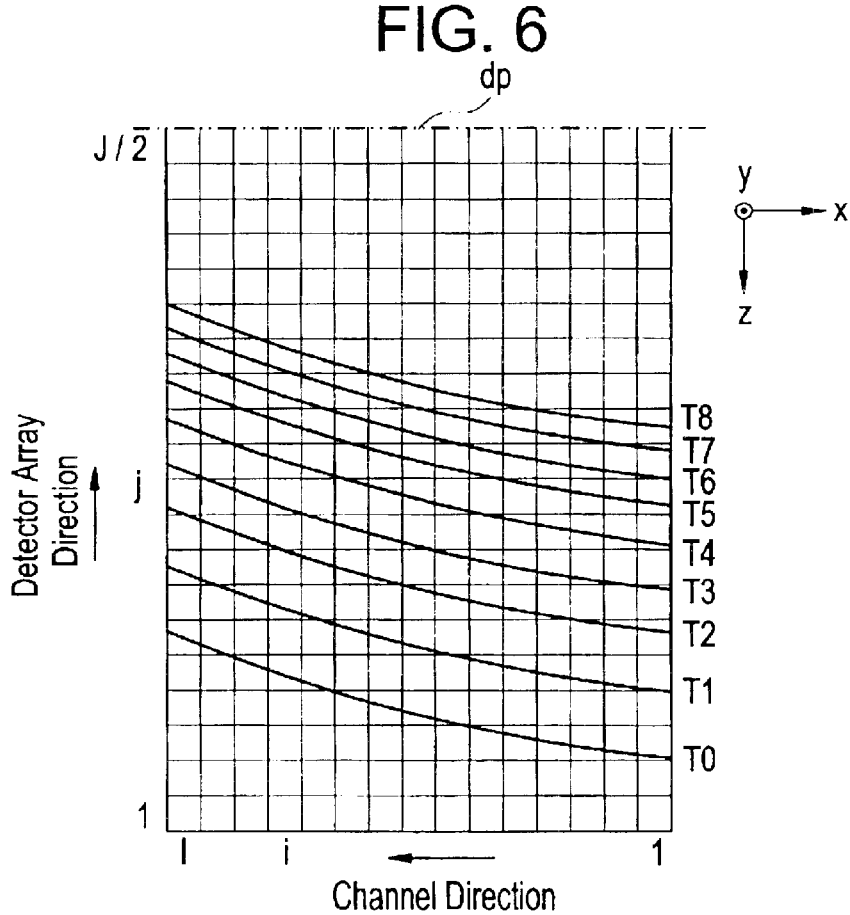
FIG. 6 shows a schematic diagram of the line projected onto the detector plane.

FIG. 6 shows lines T0 through T8, which are lines L0 through L8 projected on the detector plane detector plane in the direction of X-ray transmission, when the view in question is view=0°.

When retrieving raw data having detector array j and channel i corresponding to those lines T0 to T8, the data should be raw data Dr corresponding to those lines L0 to L8. At this point, as shown in FIG. 7, assuming lines L0' through L8, which are lines T0 through T8 projected on the projection plane pp in the direction of X-ray transmission, for raw data Dr to be developed on those lines L0' to L8.

Now referring again to FIG. 4, in step S5, cone beam reconstruction weight may be multiplied to raw data Dr for respective line of L0' to L8 so as to generate projected line data Dp, as shown in FIG. 8.

Here the cone beam reconstruction weight may be $(r1/r0)^2$, where r0 is the distance from the focal point of the X-ray tube 21 to the detector array j, channel i of the multidetector 24 corresponding to the raw data Raw data Dr; r1 is the distance from the focal point of the X-ray tube 21 to the point on the reconstruction field corresponding to the raw data Dr.

In step S6, filtering of the projected line data Dp will be carried out. More specifically, this step performs FFT on the projected line data Dp to multiply a filter function (reconstruction function) therewith and then to perform reverse FFT to yield image positional line data Df, as shown in FIG. 9.

In step S7, interpolation will be carried out on the positional line data Df of an image in the direction of lines to generate high density positional line data Dh of an image as shown in FIG. 10.

The data density of the high density positional line data Dh of an image should be 8 through 32 times of the maximum number of pixels in the reconstruction field in the direction of lines. For example, when the number of pixels in the reconstruction field P is 512 by 512 and if the power is 16, then the data density should be 8192 dots/line.

In step S8, the high density image positional line data Dh will be sampled and interpolated and/or extrapolated as needed to obtain back projection data D2 of pixels on the lines L0 to L8, as shown in FIG. 11.

In step S9, the high density image positional line data Dh will be sampled and interpolated and/or extrapolated to obtain back projection data D2 of pixels between lines L0 to L8 as shown in FIG. 12.

In FIGS. 7 to 12, while a view angle is assumed to be $-45° \leq \text{view} < 45°$ (or a view angle range mainly composed thereof and including therearound) and $135° \leq \text{view} < 225°$ (or a view angle range mainly composed thereof and including therearound), a view angle in the range of $45° \leq \text{view}$ 135° (or a view angle range mainly composed thereof and including therearound) and of $225° \leq \text{view} < 315°$ (or a view angle range mainly composed thereof and including therearound) will be as shown in FIGS. 13 to 18.

Figure 19:
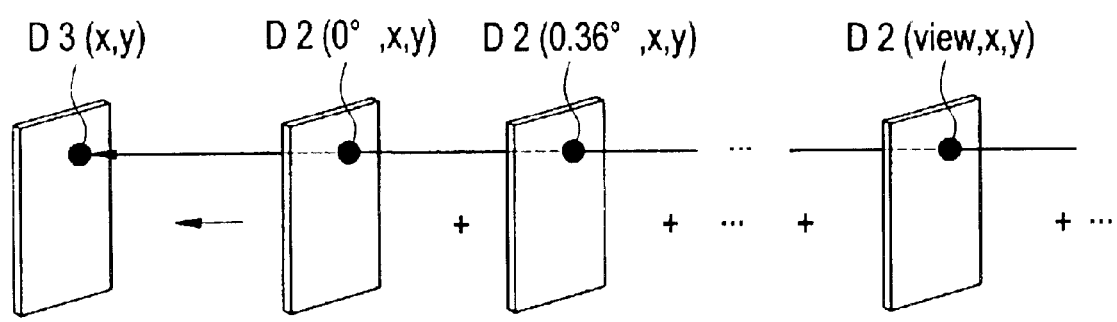
FIG. 19 shows a schematic diagram of the acquisition of back projection data D3 by adding all views of back projection pixel data D2 for each pixel.

Now returning to FIG. 4, in step S10, back projection data D2 shown in FIG. 12 or FIG. 18 will be added for each pixel, as shown in FIG. 19.

In step S11, steps S3 through S10 will be iteratively repeated for every view required to reconstruct a CT image (more specifically, views for 360° or views for 180° plus fan angle) to obtain back projection data D3 (x, y).

In step S12, postprocessing will be carried out to the back projection data D3 (x, y) to obtain a CT image.

According to X-ray CT apparatus 100 of first preferred embodiment, The amount of FFT computation may be significantly decreased since raw data Raw data Dr corresponding to those line L0 to L8 are extracted and filtering S6 is carried out only thereto. For example, the number of lines is 9, only 9 FFT computations may be sufficient for each view.

By appropriately selecting the number of lines at an interval of plural pixels, degradation of image quality may be minimized to a negligible level. In general, the preferable number of lines to make a good balance between the shortening effect of computation time and the degradation of image quality may be selected from the range from 1/512 to 1/1 of the maximum number of pixels in the reconstruction field in the direction perpendicular to the lines, more preferably from 1/64 to 1/2.

Figure 20:
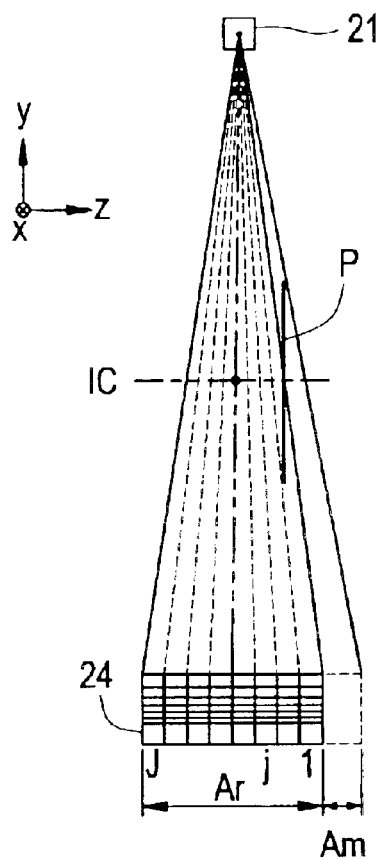
FIG. 20 shows a schematic diagram of the generation of data absent zone.

There are cases in which data absent zone Am, where no raw data exists, may be developed external to data present zone Ar, where raw data exists corresponding to the image reconstruction field P, as shown in FIG. 20.

Figure 21:
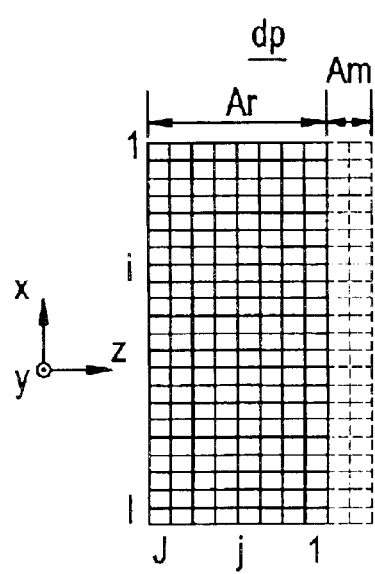
FIG. 21 shows a schematic diagram of fulfillment of data absent zone by the raw data computed by the interpolation and/or extrapolation.

In such a case, generating raw data Dr of the data absent zone Am by the extrapolation using the existing raw data, as shown in FIG. 21, may allow treating the entirety as one single detector plane dp.

If the reconstruction field P is located at the proximity of the edge of multidetector 24, in the axial scan embodiment, there may be cases in which some of raw data Dr corresponding to lines L0 to L8 are not present.

In such a case, the extrapolation of the existing raw data Dr may allow computing missing raw data Dr.

Second Embodiment

In a second embodiment, raw data of detector array j, channel i of the multidetector 24 are projected to the projection plane pp, in order to determine raw data Dr corresponding to the lines L0' to L8' projected from the lines L0 to L8 on the reconstruction field P to the projection plane pp.

In the first embodiment, in contrast, raw data Dr corresponding to the lines T0 to T8 projected from lines L0 to L8 on the reconstruction field P to the detector plane dp.

Figure 22:
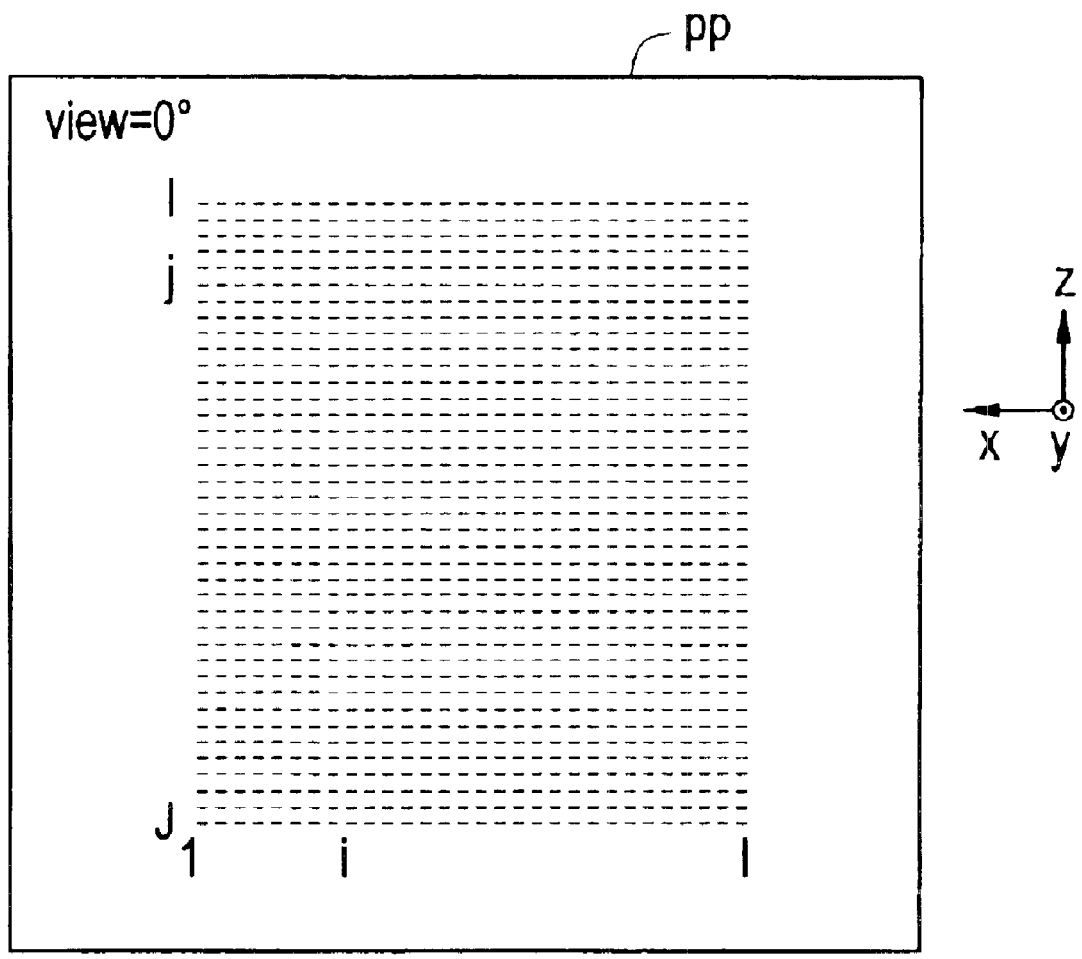
FIG. 22 shows a schematic diagram of raw data projected on the projection plane.

More specifically, raw data of detector array j, channel i of the multidetector 24 is projected onto the projection plane pp, as shown in FIG. 22.

Then, as shown in FIG. 23, lines L0 to L8 on the reconstruction field P are projected to the projection plane pp to set lines L0' to L8' as shown in FIG. 24.

Figure 25:
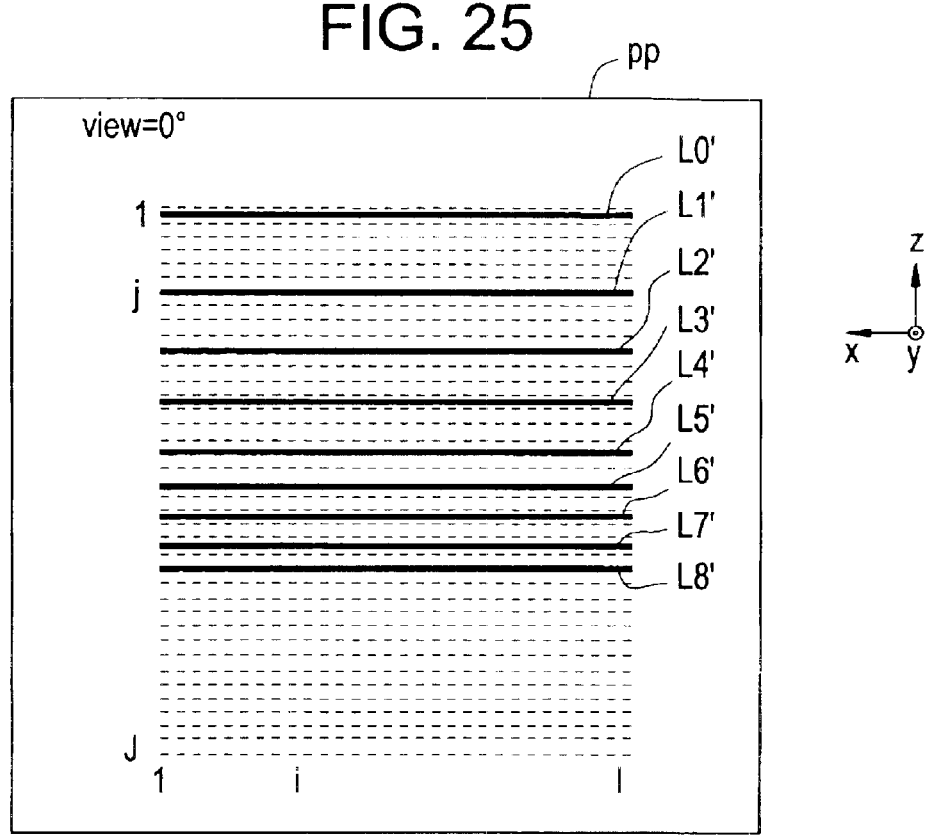
FIG. 25 shows a schematic diagram of the line projected on the projection plane.
Figure 26:
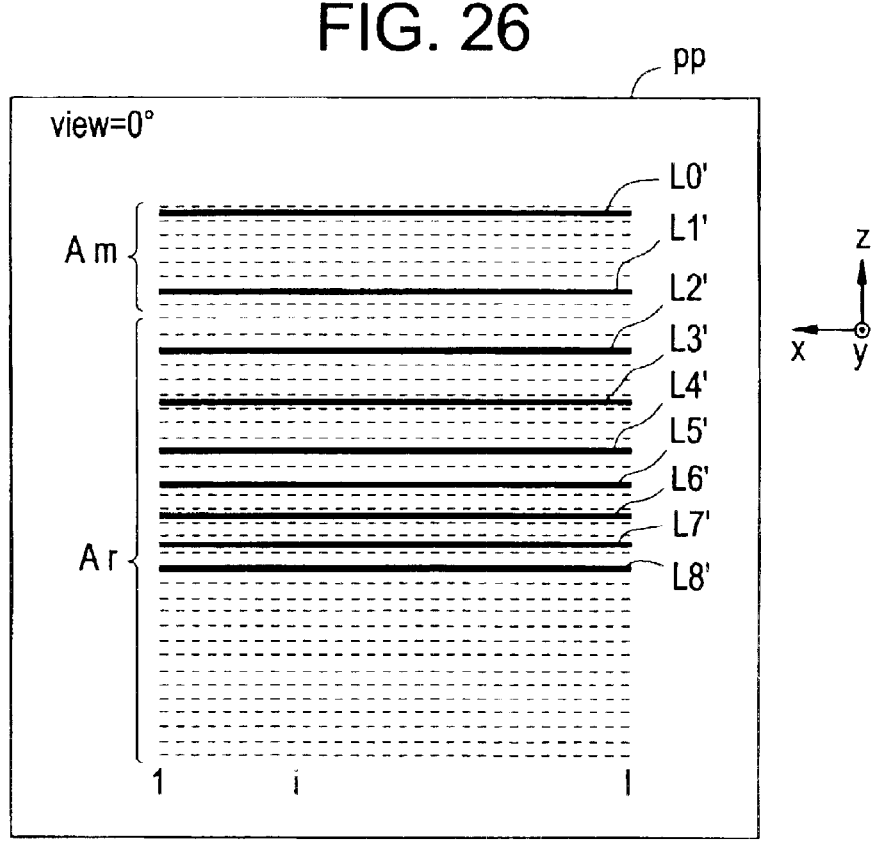
FIG. 26 shows a schematic diagram illustrating raw data projected to the projection plane (generating interpolation data) and line projected to the projection plane.

Next, as shown in FIG. 25, raw data Dr corresponding to the lines L0' to L8' may be extracted. As shown in FIG. 26, when part of lines L0' to L8' is bridging on the data absent zone Am then raw data may be computed with the extrapolation of the projection data of data present zone Ar.

After determining raw data Dr, process similar to the first embodiment may be carried out.

Third Embodiment

In a third embodiment, instead of filling all data absent zone Am with raw data Dr computed by the extrapolation, only raw data Dr on the lines corresponding to lines L0' to L8' are computed by the extrapolation.

Figure 27:
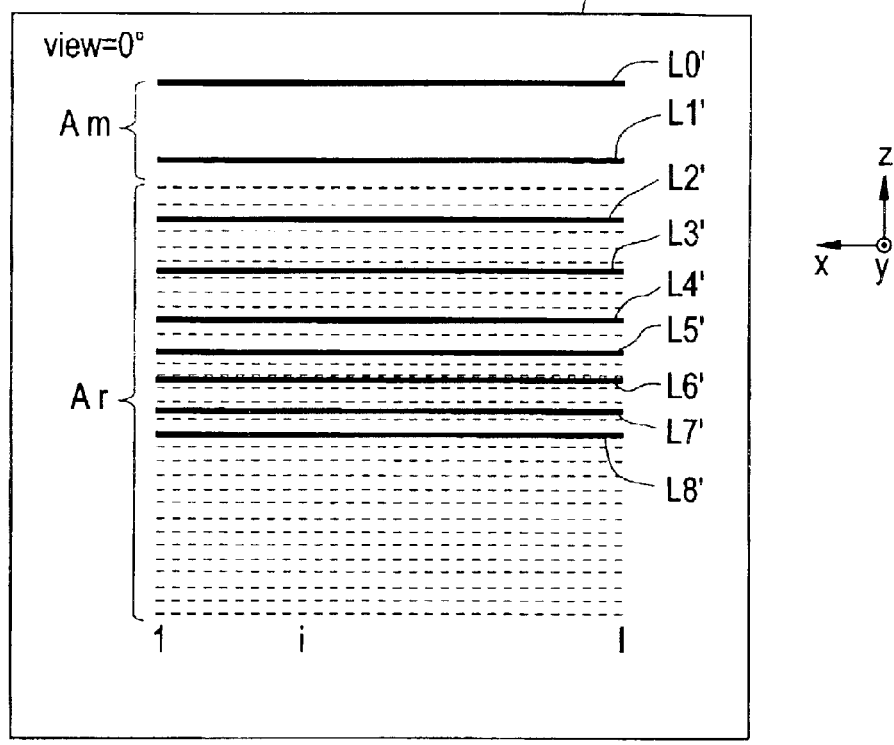
FIG. 27 shows a schematic diagram illustrating raw data projected to the projection plane (generating no interpolation data) and line projected to the projection plane.

More specifically, as shown in FIG. 27, only raw data Dr corresponding to lines L0' to L8' are computed by the extrapolation. Data absent zone Am are not all filled in with raw data Dr computed by the extrapolation.

Fourth Embodiment

In a fourth embodiment, when data absent zone Am that is required for determining raw data Dr corresponding to lines L0' to L8' is between data present zones Ar, the data absent zone Am will be filled with raw data Dr computed by the interpolation and/or extrapolation.

Figure 28:
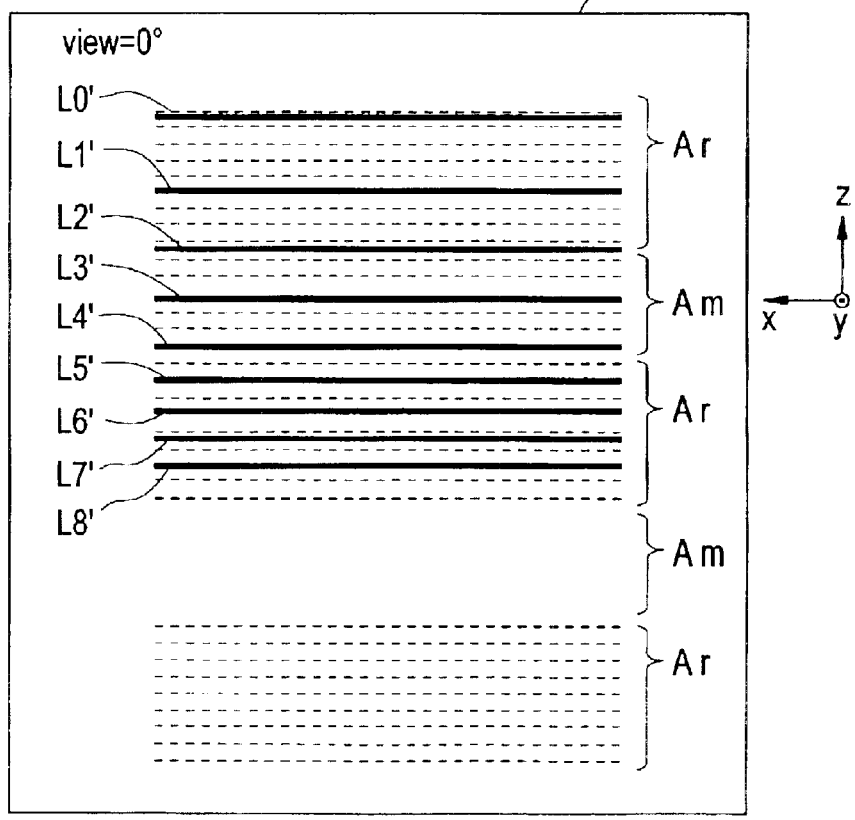
FIG. 28 shows a schematic diagram illustrating raw data projected to the projection plane (generating interpolation data when necessary) and line projected to the projection plane.

More specifically, as shown in FIG. 28, raw data Dr of the data absent zone Am required for determining raw data Dr corresponding to lines L0' to L8' will be computed with interpolation and/or extrapolation. Any other data absent zone Am not necessary for determining raw data Dr corresponding to lines L0' to L8' are not subject to the interpolation and/or extrapolation.

Fifth Embodiment

In a fifth embodiment, only data absent zone within the area corresponding to the reconstruction field P may be filled by raw data Dr computed by the interpolation and/or extrapolation.

Figure 29A:
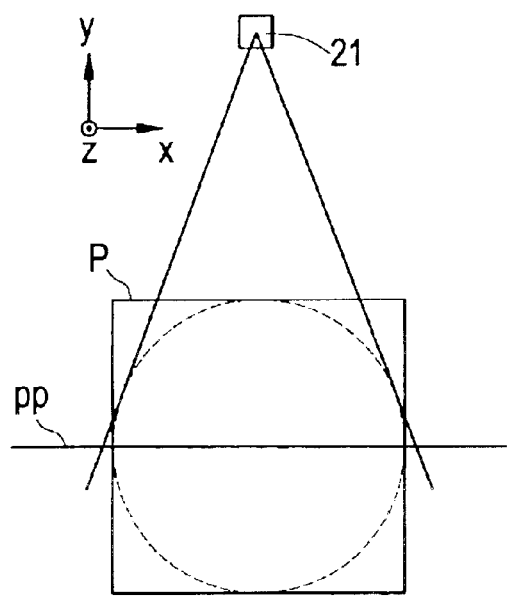
FIG. 29 shows a schematic diagram of the area projected from the reconstruction field to the projection plane.
Figure 29B:
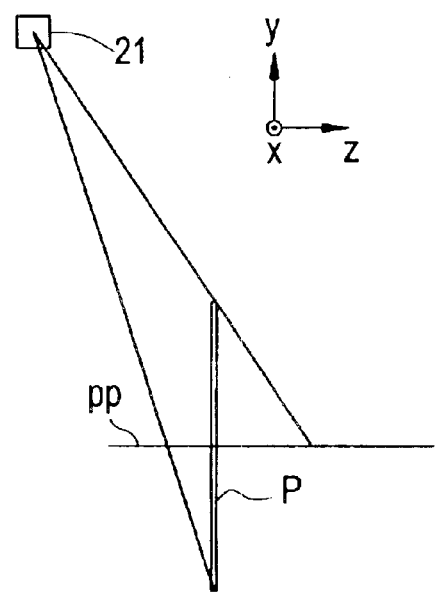
Figure 29C:
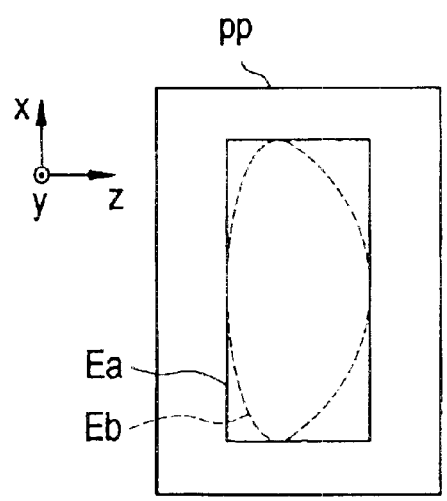

More specifically, as shown in FIG. 29, raw data Dr in the data absent zone Am included in the area Ea of the projection plane pp projected from the reconstruction field P in the direction of X-ray transmission will be computed by means of interpolation and/or extrapolation. The other data absent zone Am are not subject to interpolation and/or extrapolation.

Although in this description the reconstruction field P is assumed to be a square area circumscribing a circular area through which X-ray beam may pass at every view angles, it may be possible for the circular area to be the reconstruction field to compute raw data Dr of the data absent zone Am included in the area Eb projected from this circular area to the projection plane pp in the direction of X-ray transmission by means of interpolation and/or extrapolation so as not to apply interpolation and/or extrapolation to the other data absent zone Am.

Sixth Embodiment

In a sixth embodiment, high density raw data may be generated in the direction of detector array of the multidetector 24 by means of interpolation and/or extrapolation to make use of such high density raw data for a reconstruction field at a different location.

Figure 30:
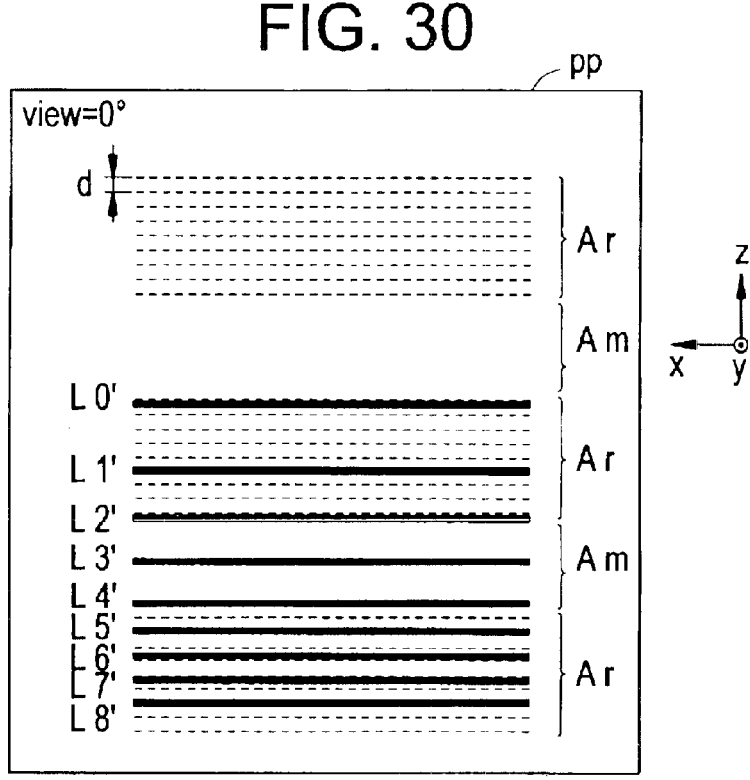
FIG. 30 shows a schematic diagram illustrating raw data projected to the projection plane (generating no interpolation data) and line projected to the projection plane.

More specifically, as shown in FIGS. 28 and 30, when the reconstruction field is located differently, the lines L0' to L8' may be located in a different position. For this reason raw data determined in a reconstruction field may not be used in another reconstruction field.

Figure 31:
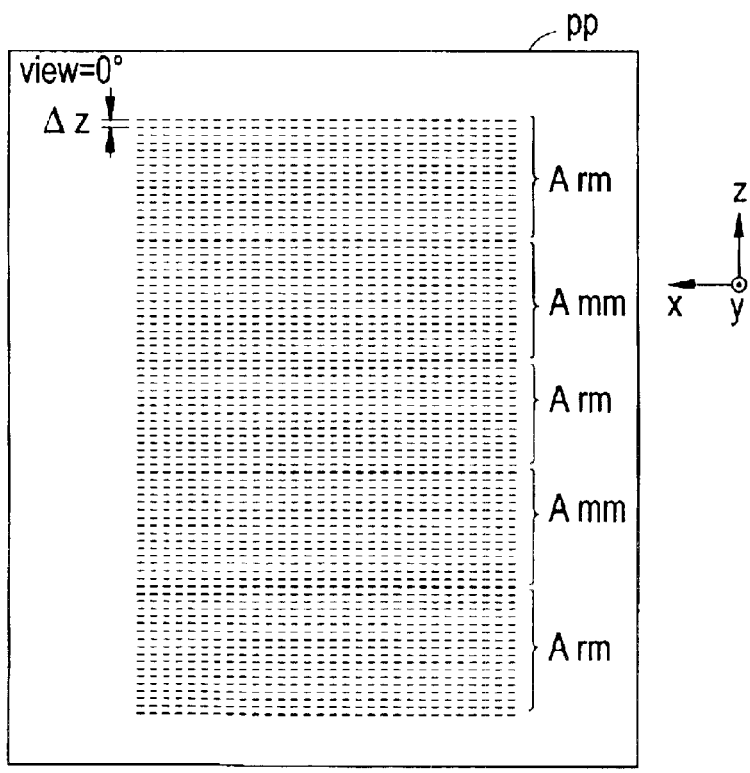
FIG. 31 shows a schematic diagram of the raw data that has high density in the detector area by the interpolation and/or extrapolation of raw data projected to the projection plane.

To solve this, as shown in FIG. 31, high density raw data may be generated by means of interpolation and/or extrapolation in the direction of detector array (z axis). At this point high density raw data may be such that the data has a density (the reverse of $\Delta z$ in FIG. 31) of twice to four times higher than the density (the reverse of d in FIG. 30) of actually present raw data in the direction of detector array.

Then to reconstruct a CT image of a reconstruction field, sampling allows obtaining raw data Dr corresponding to the lines L0' to L8' of the reconstruction field.

Seventh Embodiment

In a seventh embodiment, the number m of a plurality of lines may be varied according to the distance $\Delta z$ from the center of detector array of the multidetector 24 to the reconstruction field P.

Figure 32:
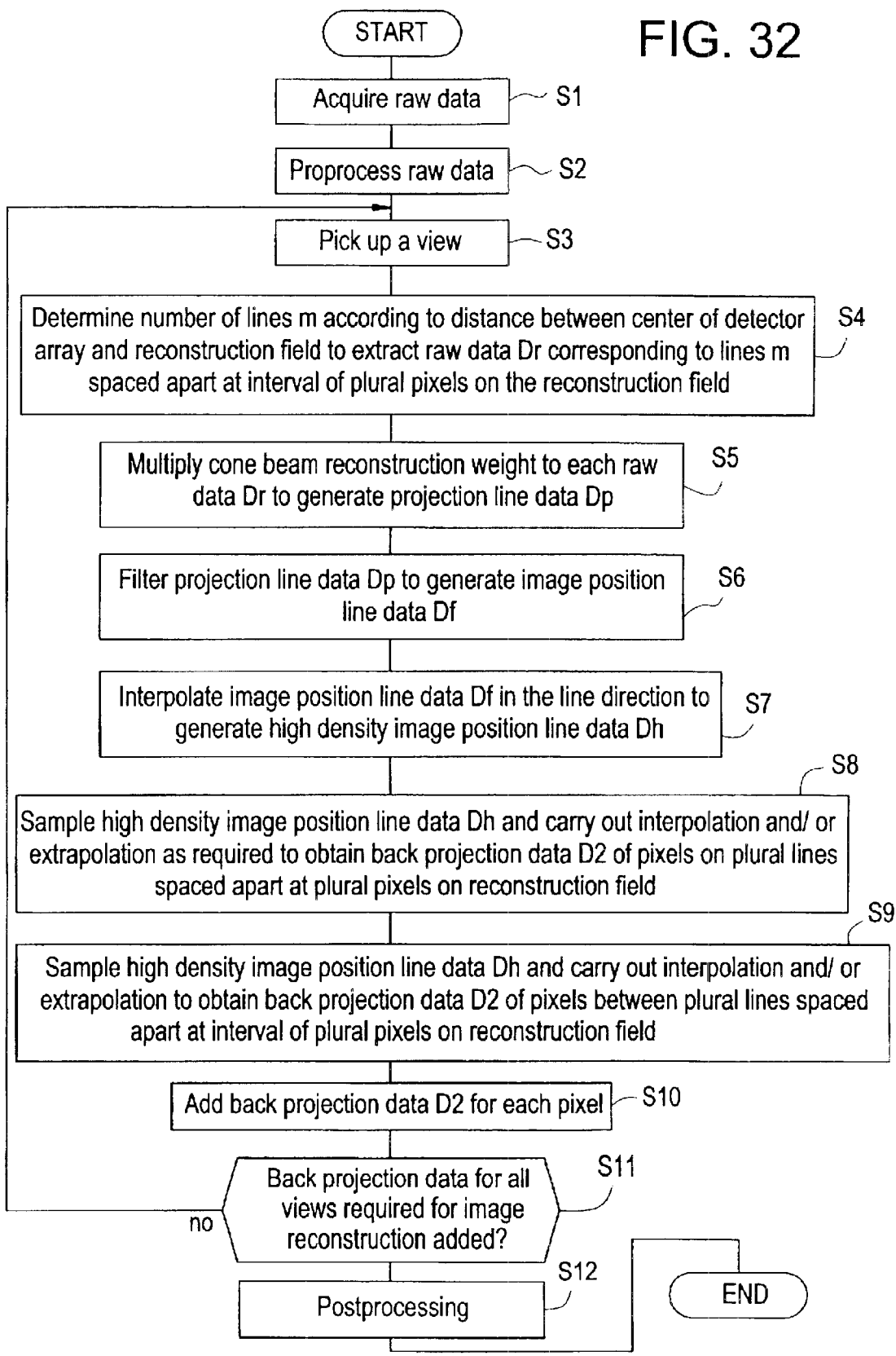
FIG. 32 shows a schematic flow diagram of the operation of X-ray CT apparatus according to a seventh embodiment.

FIG. 32 shows a schematic flow diagram illustrating overview of the operation of an X-ray CT apparatus according to the seventh embodiment.

This flow is identical to that of FIG. 4 except for the step S4' instead of step S4 of FIG. 4. Now only step S4' will be described below.

In step S4', the number of lines m according to the distance Δz (view) from the detector array of the multidetector 24 to the reconstruction field P in the view in question is first determined, then raw data Dr corresponding to parallel m lines spaced apart at an interval of plural pixels on the reconstruction field P from within raw data set.

Figure 33:
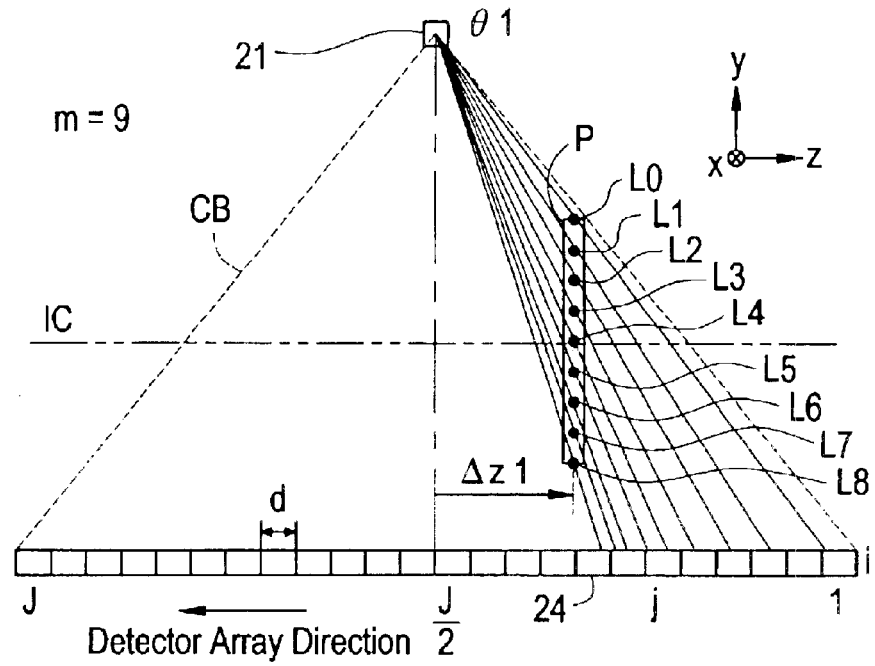
FIG. 33 shows a schematic diagram of the appropriate number of lines.

FIG. 33 shows the number of lines m=9, which is appropriate when Δz=Δz1.

With this number of lines, the line density having lines L0 to L8 on the reconstruction field P projected onto the detector plane dp of the multidetector 24 will be just optimal.

Figure 34:
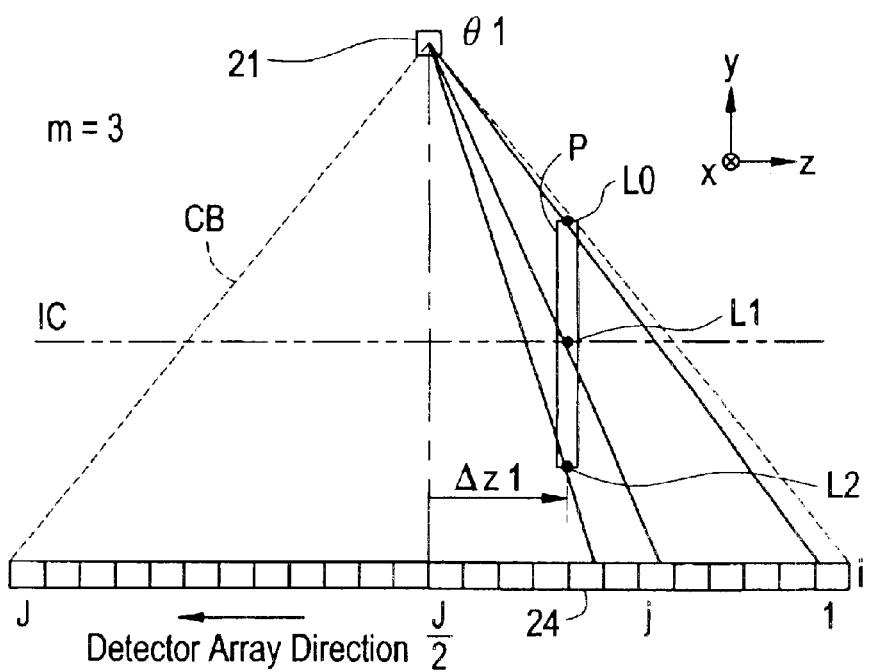
FIG. 34 shows a schematic diagram of too much inferior number of lines.

In FIG. 34 another example of inappropriate number of lines m=3 when Δz=Δz1 is illustrated.

With this number of lines, the line density having lines L0 to L2 on the reconstruction field P projected onto the detector plane dp of the multidetector 24 will be inappropriate (lines closer each to another).

Figure 35:
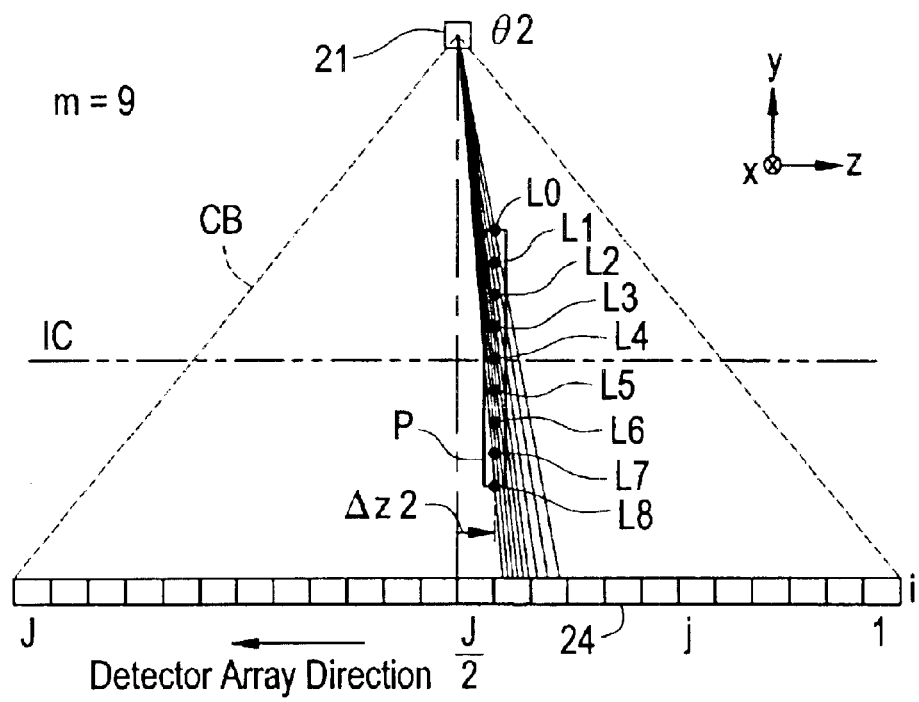
FIG. 35 shows a schematic diagram of excessively superior number of lines.

In FIG. 35 an appropriate number of lines m=9 for Δz=Δz2 is illustrated.

In this case, the line density may be inappropriate when the lines L0 to L8 on the reconstruction field P are projected to the detector plane dp of the multidetector 24 (lines too closer each to other).

Figure 36:
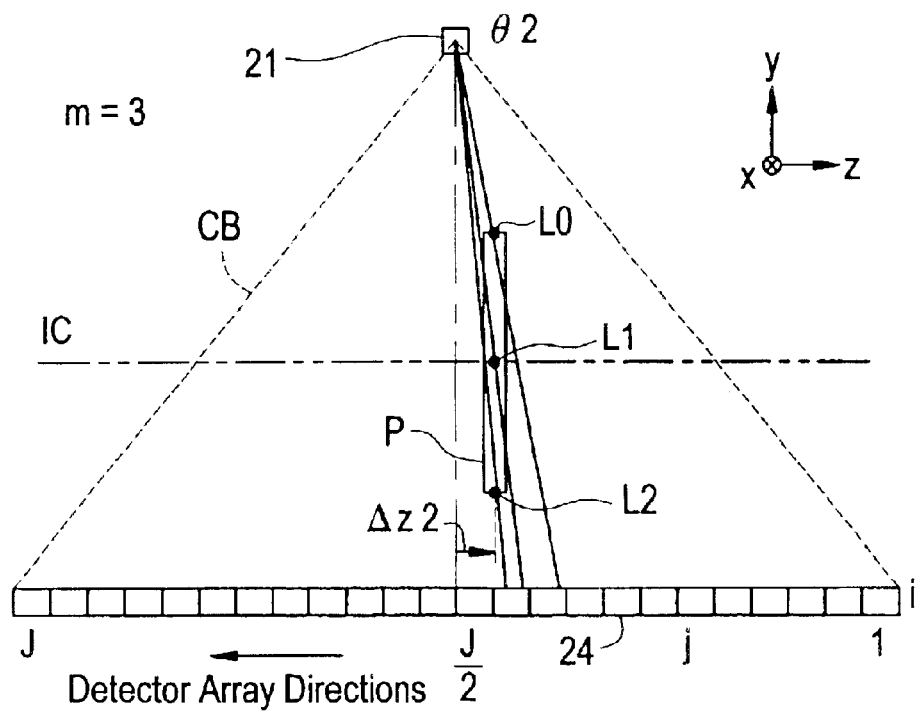
FIG. 36 shows a schematic diagram of appropriate number of lines.

In FIG. 36 an appropriate number of lines m=3 for Δz=Δz2 is illustrated.

In this case, the appropriate line density may be that the lines L0 to L2 on the reconstruction field P are projected to the detector plane dp of the multidetector 24.

Figure 37:
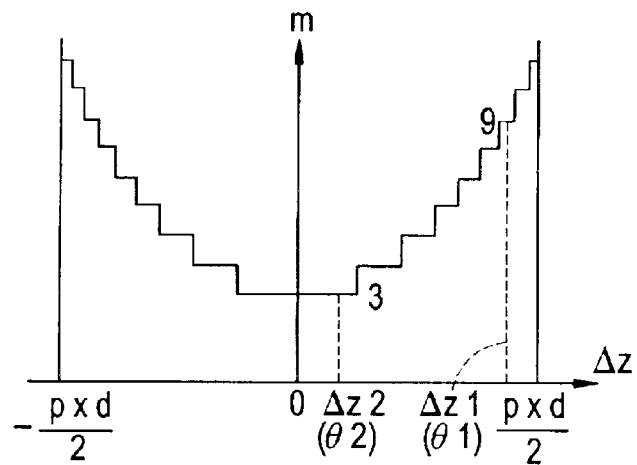
FIG. 37 shows a schematic diagram illustrating the relationship between the distance and the number of lines for standard image quality.

FIG. 37 illustrates an exemplary number of lines m determined according to the distance Δz when an operator specifies "standard quality" via input device 2.

In the figure p designates to the helical pitch, and d denotes to the detector width in the direction of detector array.

Figure 38:
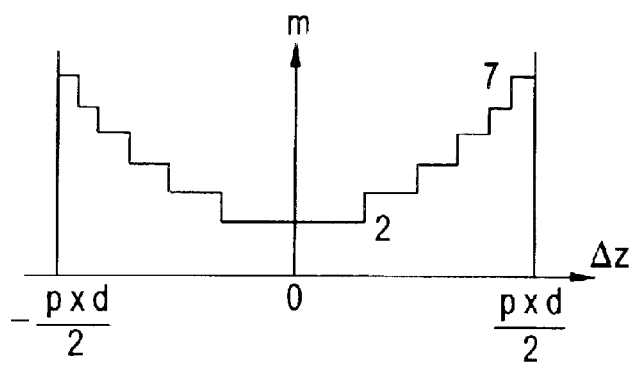
FIG. 38 shows a schematic diagram illustrating the relationship between the distance and the number of lines for lower image quality.

FIG. 38 illustrates an exemplary number of lines m determined according to the distance Δz when an operator specifies "low quality" via input device 2.

Figure 39:
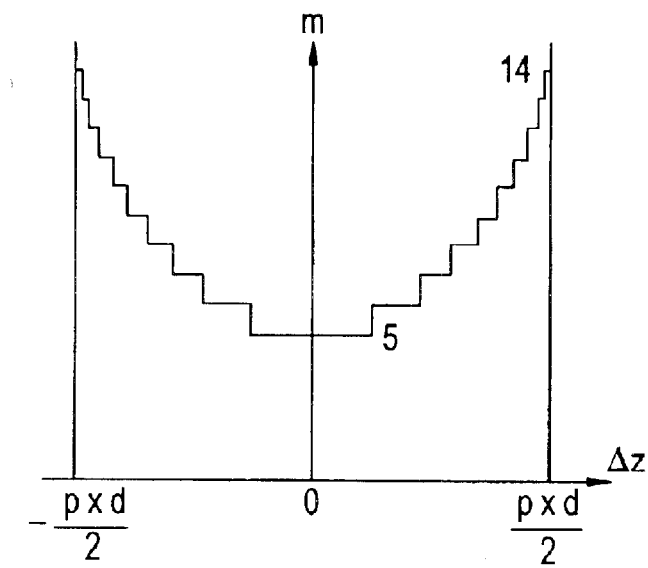
FIG. 39 shows a schematic diagram illustrating the relationship between the distance and the number of lines for higher image quality.

FIG. 39 illustrates an exemplary number of lines m determined according to the distance Δz when an operator specifies "high quality" via input device 2.

According to the X-ray CT apparatus of the seventh embodiment, since raw data Dr corresponding only to the lines of the number m is extracted and the filtering S6 is carried out solely thereto, the amount of FFT computation in filtering may be significantly decreased. Also, the number m of lines may be increased for larger distance Δz, while the number m may be decreased for smaller distance Δz, such that the optimal amount of FFT computation may be achieved in conjunction with the distance Δz for each view in the helical scan, as well as that the optimal amount of FFT computation may be achieved in correspondence with the position in the reconstruction field in the axial scan. In addition, the number m of lines may be adjusted in consideration with the image quality specified by the operator, so that the image quality and computation time may be controlled to be optimal.

Eighth Embodiment

In an eighth embodiment, the axial scan is assumed such that the number m of a plurality of lines may be varied according to the view when the reconstruction field P is offset from the revolution center IC.

Figure 40:
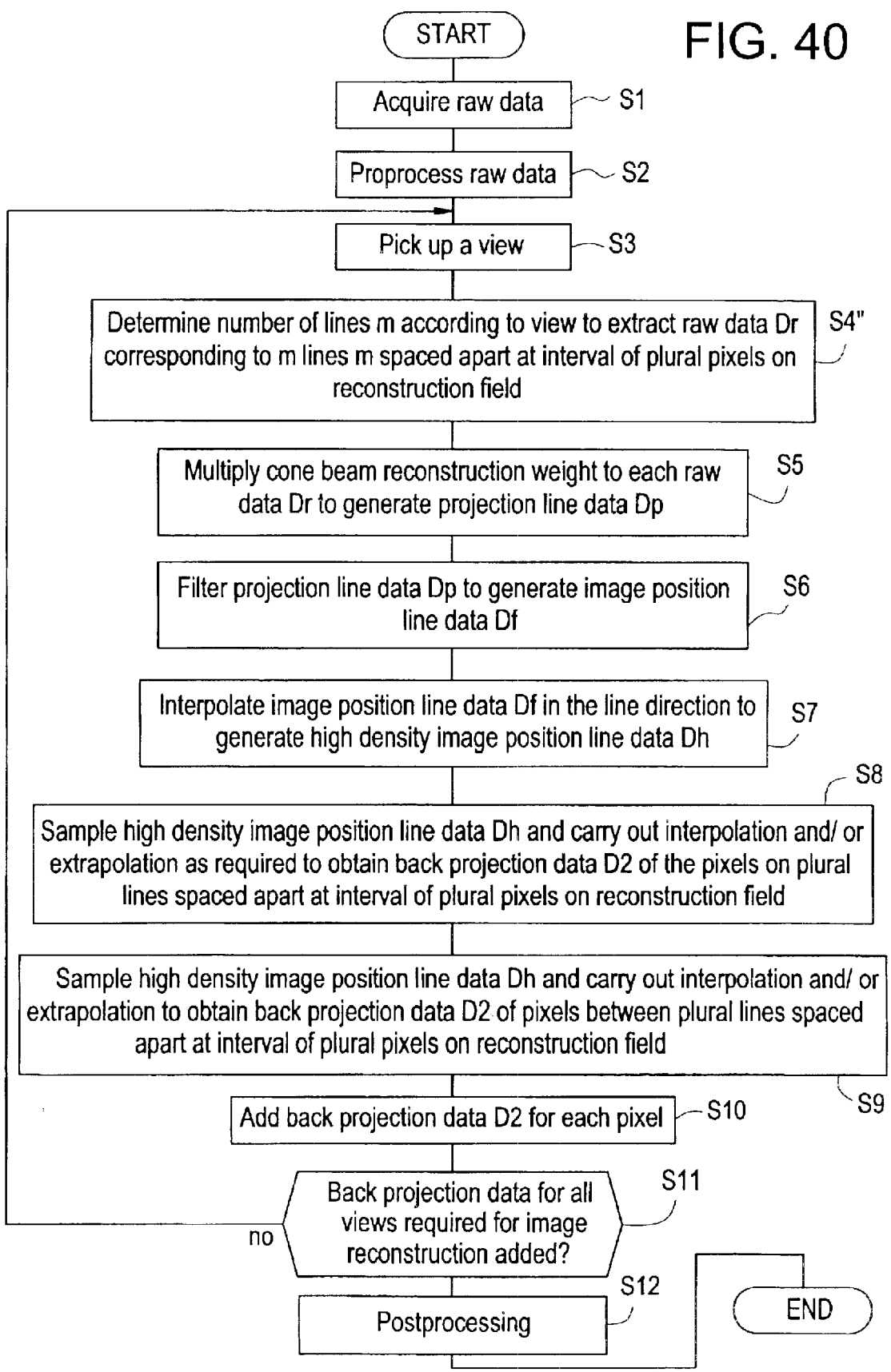
FIG. 40 shows a schematic flow diagram of the operation of X-ray CT apparatus according to an eighth embodiment.

In FIG. 40, there is depicted a schematic flow diagram illustrating the overview of operation of the X-ray CT apparatus according to the eighth embodiment.

The flow is identical to that of FIG. 4 except for step S4", which replaces step S4 of FIG. 4. In the following description only step S4" will be described.

In step S4", the number m of lines according to the view in question will be determined so as to extract raw data Dr corresponding to parallel m lines spaced apart at an even interval of plural pixels on the reconstruction field P from within raw data.

Figure 41:
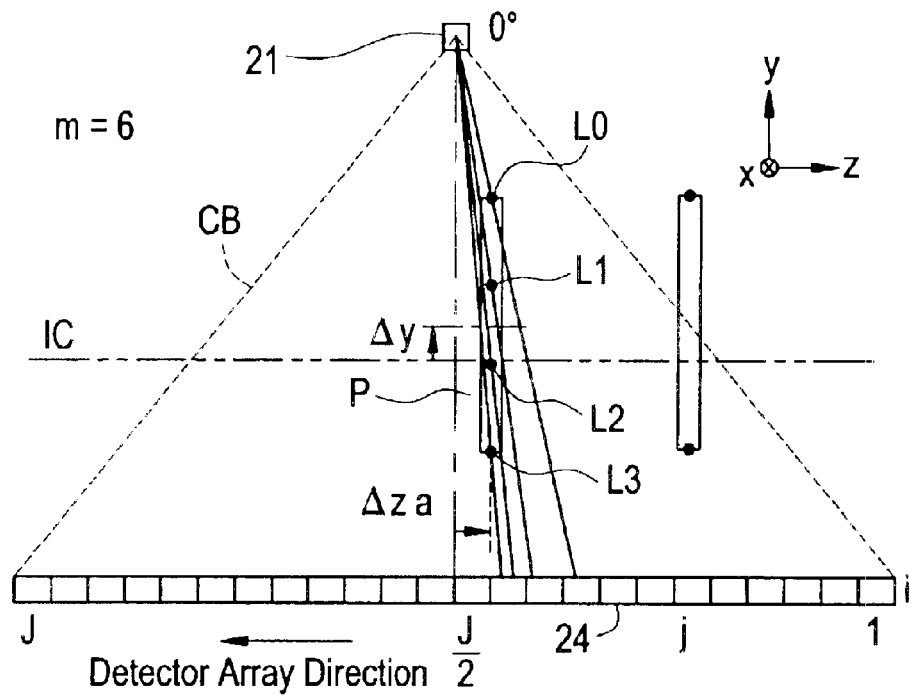
FIG. 41 shows a schematic diagram of the appropriate number of lines.
Figure 42:
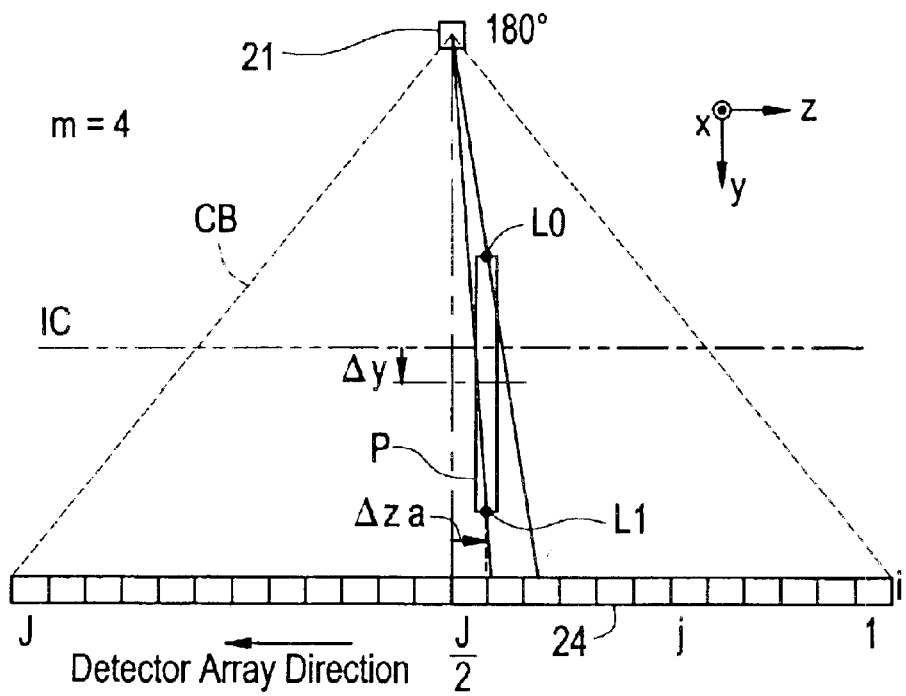
FIG. 42 shows a schematic diagram of the appropriate number of lines.

As shown in FIG. 41 and FIG. 42, the reconstruction field P is now assumed to be offset by the amount Δy in the y axis from the revolution center IC. Also the view angle, view=0° is assumed when the center axis of the cone beam CB is in parallel to y axis and the X-ray tube 21 is in the direction of offset of the reconstruction field P. Because of the axial scan, the distance Δz between the center of detector array and the reconstruction field P may be at a definitive value Δza.

In FIG. 41 an appropriate number of lines m=4 for view=0° is illustrated.

In this case, the line density may be appropriate when the lines L0 to L3 on the reconstruction field P are projected to the detector plane dp of the multidetector 24.

In FIG. 42 an appropriate number of lines m=2 for view=180° is illustrated.

In this case, the line density may be appropriate when the lines L0 to L1 on the reconstruction field P are projected to the detector plane dp of the multidetector 24.

Figure 43:
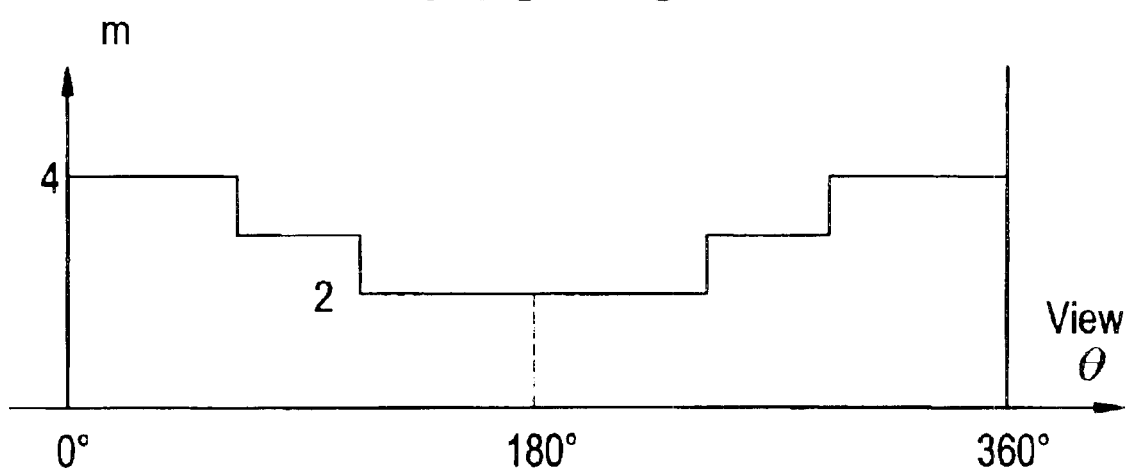
FIG. 43 shows a schematic diagram illustrating the relationship between the view and the number of lines.

FIG. 43 is a schematic diagram illustrating the number of lines m determined according to the view when the distance Δz=Δza, and the amount of offset Δy.

According to the X-ray CT apparatus of the eighth embodiment, since raw data Dr corresponding only to lines of the number m is extracted and the filtering S6 is carried out solely thereto, the amount of FFT computation in filtering may be significantly decreased. Also, the number m of lines may be increased or decreased according to the view with the offset in consideration, so that the line density when lines on the reconstruction field P are projected onto the detector plane dp of the multidetector 24 is always optimal irrespective of views to achieve the optimal amount of FFT computation.

Other Embodiments (1) In the first through sixth embodiments, "number of lines"/"number of pixels in the reconstruction field P in the direction perpendicular to the lines"=9/512≈1/57, although the number of lines m may be in the range from 1 to 512. The experiment conducted by the inventors revealed that in case where "the number of pixels in the reconstruction field P in the direction perpendicular to the lines"=512, the image quality was decreased for the number of lines≠8, on the other hand no significant change in image quality that may cause clinical problem was noticed when increasing the number of lines m to more than 65, so that the number may be preferably 9 through 65=9/512 through 65/512≈1/64 through 1/8.

(2) In the first through sixth embodiments, the number of lines m may be variable in compliance with the image quality specified. More specifically, the number m may be increased when high quality is specified and the number m may be decreased (i.e., computation decreased) when low quality is specified.

(3) Although in the seventh embodiment the number of lines m has been varied in compliance with the distance Δz and image quality specified, and in the eighth embodiment the number of lines m has been varied in compliance with the distance Δz, offset Δy and views, the number of lines m may be in general varied in compliance with, in combination, the distance Δz, offset Δy, view, and image quality specified.

(4) One of the second through sixth embodiments may be combined with either the seventh or eighth embodiment.

(5) Although in the above embodiments 512 pixels have been assumed for the reconstruction field P, the present invention may be equally applicable to any other configuration including 1024 pixels or other number of pixels.

(6) Although in the above embodiments view=0° has been assumed for the view that the center axis of cone beam CB is in parallel to y axis, any given angle may be specified for view=0°.

(7) Although in the first, seventh and eighth embodiments the line on the reconstruction field P has been projected onto the detector plane dp, in the second through sixth embodiments lines L0 to L8 have been projected to the projection plane pp, line may be projected onto the projection plane pp in the first, seventh and eighth embodiments or line L0 to L8 may be projected onto the detector plane dp in the second thorough sixth embodiments, on contrary.

(8) By extending the fifth embodiment, raw data acquisition and preprocessing may be carried out within the area corresponding to the reconstruction field P.

(9) Although in the above embodiments the reconstruction field P has been expressed as orthogonal coordinate system, the present invention may be equally applicable to the expression of polar coordinate system.

(10) Although in the above embodiments X-ray CT apparatus has been assumed to be medical use, the present invention may be equally applicable to any other type of X-ray CT apparatus for industrial use.

Many widely different embodiments of the invention may be configured without departing from the spirit and the scope of the present invention. It should be understood that the present invention is not limited to the specific embodiments described in the specification, except as defined in the appended claims.

What is claimed is:

1. A three dimensional back projection method comprising the steps of:

extracting raw data Dr each corresponding to one or a plurality of parallel lines on a reconstruction field, from within raw data gathered by an axial scan or helical scan by means of a multidetector having a plurality of detector arrays;

generating projection line data Dp by multiplying said raw data Dr by the cone beam reconstruction weight;

generating field positional line data Df of an image by performing a filter operation on said projection line data Dp;

determining back projection pixel data D2 of each pixel on the reconstruction field based on said each positional line data Df of an image; and determining a back projection data D3 by adding, for each corresponding pixel, back projection pixel data D2 of all of views used for the image reconstruction.

2. A three dimensional back projection method according to claim 1, wherein the number of said plurality of lines is in the range from 1/512 to 1/1 of the maximum number of pixels in the reconstruction field in the direction perpendicular to the lines.

3. A three dimensional back projection method according to claim 1, wherein when defining z-axis as the direction perpendicular to the revolving plane of an X-ray tube or multidetectors or as the direction of linear translation of the helical scan, y-axis as the direction of center axis of the X-ray beam at view=0°, and x-axis as the direction perpendicular to both z-axis and y-axis, x-axis becomes line direction in the range of view angle of $-45° \leq view < 45°$ or in the range mainly composed thereof and including therearound, and in the range of view angle of $135° \leq view < 225°$ or the range mainly composed thereof and including therearound, and y-axis becomes line direction in the range of view angle of $45° \leq view < 135°$ or the range mainly composed thereof and including therearound, and in the range of view angle of $225° \leq view < 315°$ or the range mainly composed thereof and including therearound.

4. A three dimensional back projection method according to claim 1, further including the steps of:

generating high density positional line data Dh of an image by interpolating or extrapolating said positional line data Df of an image in the direction of scan line; and determining back projection pixel data D2 of each pixel on the reconstruction field by sampling and interpolating and/or extrapolating when required the high density positional line data Dh of an image.

5. A three dimensional back projection method according to claim 1, further comprising the step of:

when extracting raw data Dr each corresponding to one of a plurality of parallel lines spaced apart at an even interval of a plurality of pixels on the reconstruction field from within raw data at a given view angle, if part or all of the corresponding raw data is not present, computing the corresponding raw data Dr by performing interpolation and/or extrapolation by means of adjacent raw data.

6. A three dimensional back projection method according to claim 1, further comprising the step of:

when extracting raw data Dr each corresponding to one of a plurality of parallel lines spaced apart at an even interval of a plurality of pixels on the reconstruction field from within raw data at a given view angle, if part or all of the corresponding raw data is not present, computing the raw data corresponding to said reconstruction field by performing interpolation and/or extrapolation by means of adjacent raw data to extract the raw data Dr corresponding to a plurality of lines from within thus computed raw data.

7. A three dimensional back projection method according to claim 6, wherein the field corresponding to the reconstruction field is the field to which a circular field or square field on the reconstruction plane is projected in the direction of X-ray projection.

8. A three dimensional back projection method according to claim 1, further comprising the step of:

performing interpolation and/or extrapolation of raw data in a given view angle to generate high density raw data in the direction of the detector array of multidetector; and extracting the raw data Dr corresponding to a plurality of parallel lines spaced apart at an even interval of a plurality of pixels on the reconstruction field from within said high density raw data in the direction of detector array.

9. A three dimensional back projection method according to claim 8, wherein interpolation and/or extrapolation is performed such that the raw data has the density two to four times higher than the density in the direction of detector array of raw data at a given view angle.

10. A three dimensional back projection method according to claim 1, wherein the number of lines in said plurality of lines may be varied according to the image quality specified by an operator.

11. A three dimensional back projection method according to claim 1, wherein the number of lines in said plurality of lines may be varied according to the distance from the center of said detector array to the reconstruction field.

12. A three dimensional back projection method according to claim 1, wherein the number of lines in said plurality of lines may be varied according to the view.

13. An X-ray CT apparatus comprising:
   an X-ray tube;
   a multidetector having a plurality of detector array;
   a scanner device by rotating or revolving around the object at least one of said X-ray tube or said multidetector while moving linearly both devices through a relative trajectory with respect to the object, for gathering raw data;
   a raw data extractor device for extracting raw data Dr each corresponding to one or a plurality of parallel lines on a reconstruction field from within said raw data;
   a cone beam reconstruction weight multiplier device for multiplying said raw data Dr to a cone beam reconstruction weight to generate projected line data Dp;
   a filter device for filtering said projection line data Dp to generate positional line data Df of an image;
   a back projection pixel data obtaining device for determining back projection pixel data D2 of each pixel on the reconstruction field based on the positional line data Df of an image; and
   a back projection data computing device for determining back projection data D3 by adding for each pixel back projection data D2 of all views used for reconstructing an image.

14. An X-ray CT apparatus according to claim 13, wherein the number of said plurality of lines is in the range from 1/512 to 1/1 of the maximum number of pixels in the reconstruction field in the direction perpendicular to the lines.

15. An X-ray CT apparatus according to claim 13, wherein when defining z-axis as the direction perpendicular to the revolving plane of an X-ray tube or multidetectors or as the direction of linear translation of the helical scan, y-axis as the direction of center axis of the X-ray beam at view=0°, and x-axis as the direction perpendicular to both z-axis and y-axis, x-axis becomes line direction in the range of view angle of −45°≦view<45° or in the range mainly composed thereof and including therearound, and in the range of view angle of 135°≦view<225° or the range mainly composed thereof and including therearound, and y-axis becomes line direction in the range of view angle of 45°≦view<135° or the range mainly composed thereof and including therearound, and in the range of view angle of 225°≦view<315° or the range mainly composed thereof and including therearound.

16. An X-ray CT apparatus according to claim 13, further comprising:

a line direction interpolation and/or extrapolation device for performing interpolation and/or extrapolation in the direction of lines on said positional line data Df of an image to generate high density positional line data of an image Dh; and wherein said back projection pixel data obtaining device performs sampling of said high density positional line data Dh of an image as well as interpolation and/or extrapolation to determine back projection pixel data D2 of each pixel on the reconstruction field.

17. An X-ray CT apparatus according to claim 13, further comprising:
   an interpolation and/or extrapolation processing device, for use when extracting raw data Dr corresponding to a plurality of parallel lines spaced apart at an even interval of a plurality of pixels on the reconstruction field from within raw data of a given view angle, if part or all of the corresponding raw data is not present, operable for computing the corresponding raw data Raw data Dr by performing interpolation and/or extrapolation by means of adjacent raw data.

18. An X-ray CT apparatus according to claim 13, further comprising:
   an interpolation and/or extrapolation processing device for use when extracting raw data Dr each corresponding to one of a plurality of parallel lines spaced apart at an even interval of a plurality of pixels on the reconstruction field from within raw data at a given view angle, if part or all of the raw data corresponding to the reconstruction field is not present, computing the raw data corresponding to said reconstruction field by performing interpolation and/or extrapolation by means of adjacent raw data to extract the raw data Dr corresponding to a plurality of lines from within thus computed raw data; and
   wherein said raw data extractor device extracts the raw data Dr corresponding to a plurality of lines from within said computed raw data.

19. An X-ray CT apparatus according to claim 18, wherein the field corresponding to the reconstruction field is the field to which a circular field or square field on the reconstruction plane is projected in the direction of X-ray projection.

20. An X-ray CT apparatus according to claim 13, further comprising:
   a detector array direction interpolation and/or extrapolation processing device for performing interpolation and/or extrapolation of raw data at a given view angle to generating high density raw data in the direction of detector array of the multidetector; wherein
   said raw data extracting device extracts raw data Dr corresponding to a plurality of parallel lines spaced apart at an even interval of a plurality of pixels on the reconstruction field from within the high density raw data in the direction of detector array.

21. An X-ray CT apparatus according to claim 20, wherein said detector array direction interpolation and/or extrapolation processing device performing interpolation and/or extrapolation, which is such that the raw data has the density two to four times higher than the density in the direction of detector array of raw data at a given view angle.

22. An X-ray CT apparatus according to claim 13, further comprising:
   a line count setting device for varying the number of lines in said plurality of lines according to the image quality specified by an operator.

23. An X-ray CT apparatus according to claim 13, further comprising:

a line count setting device for varying the number of lines in said plurality of lines according to the distance from the center of said detector array to the reconstruction field.

24. An X-ray CT apparatus according to claim 13, further comprising:

a line count setting device for varying the number of lines in said plurality of lines according to the view.

* * * * *

UNITED STATES PATENT AND TRADEMARK OFFICE
CERTIFICATE OF CORRECTION

PATENT NO.    : 6,865,247 B2                                              Page 1 of 1
DATED         : March 8, 2005
INVENTOR(S)   : Akira Hagiwara It is certified that error appears in the above-identified patent and that said Letters Patent is hereby corrected as shown below:

Column 19,
Line 22, delete "array" and insert therefor -- arrays --.

Column 20,
Line 20, delete "Raw data Dr" and insert therefor -- Dr --.

Signed and Sealed this

Thirtieth Day of August, 2005

JON W. DUDAS
*Director of the United States Patent and Trademark Office*